US009895432B2

(12) United States Patent
Hasumi et al.

(10) Patent No.: US 9,895,432 B2
(45) Date of Patent: Feb. 20, 2018

(54) COMPOSITIONS, METHODS AND THERAPIES FOR ADMINISTERING ANTIGEN PEPTIDE

(71) Applicant: Hasumi International Research Foundation, Washington, DC (US)

(72) Inventors: Kenichiro Hasumi, Tokyo (JP); Mikio Kuraya, Tokyo (JP)

(73) Assignee: Kenichiro Hasumi, Tokyo (JP)

( * ) Notice: Subject to any disclaimer, the term of this patent is extended or adjusted under 35 U.S.C. 154(b) by 330 days.

(21) Appl. No.: 14/312,162

(22) Filed: Jun. 23, 2014

(65) Prior Publication Data
US 2015/0023997 A1  Jan. 22, 2015

Related U.S. Application Data

(63) Continuation-in-part of application No. 13/380,425, filed as application No. PCT/JP2011/062305 on May 23, 2011, now Pat. No. 8,784,830.

(60) Provisional application No. 61/396,574, filed on May 27, 2010.

(51) Int. Cl.
| *A61K 39/05* | (2006.01) |
| *C07K 14/195* | (2006.01) |
| *C12N 15/31* | (2006.01) |
| *C12Q 1/68* | (2006.01) |
| *C07K 16/12* | (2006.01) |
| *A61P 17/10* | (2006.01) |
| *C07K 7/08* | (2006.01) |
| *C12N 15/63* | (2006.01) |
| *A61K 39/02* | (2006.01) |
| *A61K 31/7088* | (2006.01) |
| *A61K 38/16* | (2006.01) |
| *C07K 14/36* | (2006.01) |
| *A61K 45/06* | (2006.01) |
| *A61K 39/00* | (2006.01) |

(52) U.S. Cl.
CPC ...... *A61K 39/0208* (2013.01); *A61K 31/7088* (2013.01); *A61K 38/164* (2013.01); *A61K 39/05* (2013.01); *A61K 45/06* (2013.01); *C07K 14/195* (2013.01); *C07K 14/36* (2013.01); A61K 2039/53 (2013.01); A61K 2039/55516 (2013.01); A61K 2039/55588 (2013.01); A61K 2039/58 (2013.01); A61K 2039/645 (2013.01); A61K 2039/70 (2013.01); C07K 2319/30 (2013.01)

(58) Field of Classification Search
None
See application file for complete search history.

(56) References Cited

U.S. PATENT DOCUMENTS 8,784,830 B2   7/2014 Hasumi et al.

FOREIGN PATENT DOCUMENTS

| CA | 2 407 352 A1 | 11/2001 |
| JP | 2004-520803 A | 7/2004 |
| WO | 2010/039750 A2 | 4/2010 |
| WO | 2010-065735 A2 | 6/2010 |
| WO | 2011/149099 A1 | 12/2011 |

OTHER PUBLICATIONS

Greenspan et al. (Nature Biotechnology 7: 936-937, 1999)).*
Bowie, James U., et al., "Deciphering the Message in Protein Sequences: Tolerance to Amino Acid Substitutions", Science, New Series, vol. 247, No. 4948, (Mar. 16, 1990), pp. 1306-1310.
Bruggemann, Holger, et al., "The Complete Genome Sequence of Propionbacterium Acnes, A Commensal of Human Skin", Science, 305, (2004), pp. 671-673.
Burgess, Wilson H., et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue", The Journal of Cell Biology, vol. 111, (Nov. 1990), pp. 2129-2138.
Coleman, P.M., "Effects of Amino Acid Sequence Changes on Antibody-Antigen Interactions", Res. Immunology, vol. 145, (Jan. 1995), pp. 33-36.
Kuraya, M., "Possibility of Acne Vaccine", Medical Beauty Forum, Autumn & Winter, (Feb. 7, 2010).
Lazar, Eliane, et al., "Transforming Growth Factor α : Mutation of Aspartic Acid 47 and Leucine 48 Results in Different Biological Activities", Molecular and Cellular Biology, vol. 8, No. 3, (Mar. 1998), pp. 1247-1252.
Lodes, Michael J., et al., "Variable Expression of Immunoreactive Surface Proteins of Propionibacterium Acnes", Microbiology (2006), 152, pp. 3667-3681.
Nakatsuji, Terauki, et al., "Vaccination Targeting a Surface Sialidase of P. Acnes: Implication for New Treatment of Acne Vulgaris", PLoS One, (Feb. 2008), vol. 3, Issue 2, pp. 1-9.
Ramstad, Stale, et al., "The Temperature Dependence of Porphyrin Production in Propionibacterium Acnes After Incubation With 5-Aminolevulinic Acid (ALA) and Its Methyl Ester (m-ALA)", Photochemical & Photobiological Sciences, (2006), 5, pp. 66-72.
SubName: Full=Outer membrane . . . , XP002675395, retrieved from EBI accession No. UNIPROT: Unreviewed, Sep. 13, 2004, Database accession No. Q6A6X7.
SubName: Full=Conserved membrane . . . , XP002675396, retrieved from EBI accession No. UNIPROT: Unreviewed, Sep. 13, 2004, Database accession No. Q6A5A4.

(Continued)

Primary Examiner — Robert A Zeman
(74) Attorney, Agent, or Firm — Eckert Seamans Cherin & Mellott, LLC; Carol A. Marmo

(57) ABSTRACT

The invention relates to compositions, methods and therapies for the treatment of inflammation caused by infection with *Propionibacterium acnes*. The compositions include a combination of peptide and anti-TNF. The peptide consists of a specific amino acid sequence or a peptide consisting of an amino acid sequence derived the specific amino acid sequence by deletion, substitution, insertion or addition of one or more amino acids. The administration of the peptide and anti-TNF in therapeutically effective amounts to a patient is effective to suppress, by immune response, inflammation caused by infection with *Propionibacterium acnes*.

5 Claims, 8 Drawing Sheets

(56) References Cited

OTHER PUBLICATIONS

International Searching Authority, International Search Report and the Written Opinion for International Application No. PCT/US15/37075, dated Dec. 4, 2015.

Campione, "Severe Acne Successfully Treated With Etanercept", Ada Derm Venereol 86, Acta Dermato-Venereologica ISSN 0001-5555, 2006.

Hampton, "Successful treatment of resistant SAPHO syndrome with anti-TNF therapy", BMJ Case Reports, 2013.

* cited by examiner

FIG. 6

| BACTERIAL STRAINS | No. | sequence | | | | |
|---|---|---|---|---|---|---|
| SEPARATED BACTERIAL STRAINS (SEQ NO.16) | 4 | GTTTGATCCT | GGCTCAGGAC | GAACGCTGGC | GGCGTGCTTA | ACACATGCAA |
| ATCC 6919 (SEQ NO. 8) | 1 | AGA GTTTGATCCT | GGCTCAGGAC | GAACGCTGGC | GGCGTGCTTA | ACACATGCAA |
| SEPARATED BACTERIAL STRAINS | 54 | GTCGAACGGA | AAGGCCCTGC | TTTTGTGGGG | TGCTCGAGTG | GCGAACGGGT |
| ATCC 6919 | 54 | GTCGAACGGA | AAGGCCCTGC | TTTTGTGGGG | TGCTCGAGTG | GCGAACGGGT |
| SEPARATED BACTERIAL STRAINS | 104 | GAGTAACACG | TGAGTAACCT | GCCCTTGACT | TTGGGATAAC | TTCAGGAAAC |
| ATCC 6919 | 104 | GAGTAACACG | TGAGTAACCT | GCCCTTGACT | TTGGGATAAC | TTCAGGAAAC |
| SEPARATED BACTERIAL STRAINS | 154 | TGGGGCTAAT | ACCGGATAGG | AGCTCCTGCT | GCATGGTGGG | GGTTGGAAAG |
| ATCC 6919 | 154 | TGGGGCTAAT | ACCGGATAGG | AGCTCCTGCT | GCATGGTGGG | GGTTGGAAAG |
| SEPARATED BACTERIAL STRAINS | 204 | TTTCGGCGGT | TGGGGATGGA | CTCGCGGCTT | ATCAGCTTGT | TGGTGGGGTA |
| ATCC 6919 | 204 | TTTCGGCGGT | TGGGGATGGA | CTCGCGGCTT | ATCAGCTTGT | TGGTGGGGTA |
| SEPARATED BACTERIAL STRAINS | 254 | GTGGCTTACC | AAGGCTTTGA | CGGGTAGCCG | GCCTGAGAGG | GTGACCGGCC |
| ATCC 6919 | 254 | GTGGCTTACC | AAGGCTTTGA | CGGGTAGCCG | GCCTGAGAGG | GTGACCGGCC |
| SEPARATED BACTERIAL STRAINS | 304 | ACATTGGGAC | TGAGATACGG | CCCAGACTCC | TACGGGAGGC | AGCAGTGGGG |
| ATCC 6919 | 304 | ACATTGGGAC | TGAGATACGG | CCCAGACTCC | TACGGGAGGC | AGCAGTGGGG |
| SEPARATED BACTERIAL STRAINS | 354 | AATATTGCAC | AATGGGCGGA | AGCCTGATGC | AGCAACGCCG | CGTGCGGGAT |
| ATCC 6919 | 354 | AATATTGCAC | AATGGGCGGA | AGCCTGATGC | AGCAACGCCG | CGTGCGGGAT |
| SEPARATED BACTERIAL STRAINS | 404 | GACGGCCTTC | GGGTTGTAAA | CCGCTTTCGC | CTGTGACGAA | GCGTGAGTGA |
| ATCC 6919 | 404 | GACGGCCTTC | GGGTTGTAAA | CCGCTTTCGC | CTGTGACGAA | GCGTGAGTGA |
| SEPARATED BACTERIAL STRAINS | 454 | CGGTAATGGG | TAAAGAAGCA | CCGGCTAACT | ACGTGCCAGC | AGCCGCGGTG |
| ATCC 6919 | 454 | CGGTAATGGG | TAAAGAAGCA | CCGGCTAACT | ACGTGCCAGC | AGCCGCGGTG |
| SEPARATED BACTERIAL STRAINS | 504 | ATAC | | | | |
| ATCC 6919 | 504 | ATAC GTAG | | | | |

# COMPOSITIONS, METHODS AND THERAPIES FOR ADMINISTERING ANTIGEN PEPTIDE

CROSS-REFERENCE TO RELATED APPLICATIONS

This application is a continuation-in-part application and claims priority from U.S. patent application Ser. No. 13/380,425 filed Dec. 22, 2011, entitled "Antigen Peptide and Use Thereof", which issued as U.S. Pat. No. 8,784,830, on Jul. 22, 2014, from PCT International Application PCT/JP2011/062305 entitled "Antigen Peptide and Use Thereof"filed May 23, 2011, and from Provisional Application 61/396,574, entitled "Antigen Peptide and Use Thereof"filed on May 27, 2010. These references are hereby incorporated in their entirety by reference.

FIELD OF THE INVENTION

The invention relates generally to antigen peptides and their use against *Propionibacterium acne*. The invention further includes the combination of antigen peptides and anti-tumor necrosis factor (anti-TNF), and the use thereof against *Propionibacterium acne*. The invention also relates to methods and therapies for treating a patient having *Propionibacterium acne*. More particularly, the invention includes administering antigen peptide and anti-TNF to a patient in therapeutically effective amounts.

BACKGROUND OF THE INVENTION

Acne is a known inflammatory disease that often appears on portions of a patient extending from the neck to the face of the human body. Typically, acne is most prevalent during puberty, however, it is known that the presence of acne can be found during adulthood as well. Due to the inflammation occurring on portions of the human body which are exposed and visible, acne may have a significant psychological influence on the person inflicted with this disease.

Various therapeutic agents for acne have been developed. In particular, there have been drugs developed which directly act on *Propionibacterium acnes* that is a pathogen of acne.

In the art, the complete genome sequence of *Propionibacterium acnes* has been determined and as a result, it is known that many genes of *Propionibacterium acnes* encode a virulence factor. Based on this information, research on sialidase of *Propionibacterium acnes* has been carried out in developing a vaccine.

Tumor necrosis factor (TNF) is a cytokine which circulates throughout the body. TNF is critical for effective immune surveillance and is required for proper proliferation and function of natural killer cells, T cells, B cells, macrophages, and dendritic cells. The primary role of TNF is in the regulation of immune cells. It is known that TNF can cause systemic inflammation which can result in various chronic conditions. Anti-TNF, also known as TNF blockers or inhibitors, interferes with the body's production of TNF and as a result, is effective to reduce inflammation.

Most drugs that have been developed to treat *Propionibacterium acnes* act on bacterial cells of *Propionibacterium acnes* that are a cause of acne and exert an anti-inflammatory effect. Accordingly, in a situation where there is reinfection with *Propionibacterium acnes*, inflammation occurs again. Thus, the use of such drugs may be effective temporarily, but their use induces the emergence of a drug-resistant bacterium which makes treatment more difficult.

There is a need in the art to develop antigen peptides against *Propionibacterium acnes*, as well as therapies and methods of administering the antigen peptides to regress, reduce or eliminate *Propionibacterium acnes* in a patient, and more particularly, therapies and methods which enable the continuous treatment of acne. It is desirable for the therapies and methods of administration to be effective in a reasonable period of time. A continuous treatment of acne includes immunotherapy, that is, a vaccine. Without intending to be bound by any particular theory, it is believed that establishing effective anti-acne immunity (recognition and immunologic memory of specific *Propionibacterium acnes*), can result in the immediate elimination of *Propionibacterium acnes* at least on reinfection with strains of the same *Propionibacterium acnes*. Accordingly, it is reasonably expected that immunotherapy can exert a continuous anti-inflammatory effect.

In accordance with the invention, it has been found that a peptides consisting of an amino acid sequence and anti-TNF can efficiently suppress inflammation induced by *Propionibacterium acnes* in patients.

SUMMARY OF THE INVENTION

In one aspect, the invention solves the above needs by providing a composition which includes peptide and anti-TNF. The peptide includes one or more of: (a) a peptide consisting of an amino acid sequence indicated by SEQ NO. 1, (b) a peptide consisting of an amino acid sequence derived from the amino acid sequence indicated by SEQ NO. 1 by deletion, substitution, insertion, or addition of one or several amino acids, (c) a peptide consisting of an amino acid sequence indicated by SEQ NO. 3, and (d) a peptide consisting of an amino acid sequence derived from the amino acid sequence indicated by SEQ NO. 3 by deletion, substitution, insertion, or addition of one or several amino acids.

The peptide present in the composition can include: (e) a peptide which is in a form of a multivalent antigen peptide obtained by binding a plurality of peptides described in the above (a) or (b) by a linker, and (f) a peptide which is in a form of a multivalent antigen peptide obtained by binding a plurality of peptides described in the above (c) or (d) by a linker.

In another aspect, the invention provides a method of suppressing inflammation caused by infection with *Propionibacterium acnes* in a patient. The method includes introducing into the patient peptide and anti-TNF. The peptide includes one or more of: (a) a peptide consisting of an amino acid sequence indicated by SEQ NO. 1, (b) a peptide consisting of an amino acid sequence derived from the amino acid sequence indicated by SEQ NO. 1 by deletion, substitution, insertion, or addition of one or several amino acids, (c) a peptide consisting of an amino acid sequence indicated by SEQ NO. 3, and (d) a peptide consisting of an amino acid sequence derived from the amino acid sequence indicated by SEQ NO. 3 by deletion, substitution, insertion, or addition of one or several amino acids.

In certain embodiments, the peptide and anti-TNF are introduced simultaneously into the patient. The peptide and the anti-TNF can be combined to form a composition and the composition can be introduced into the patient. In other embodiments, the peptide and the anti-TNF can be introduced separately into the patient. The peptide and the anti-TNF can be introduced sequentially into the patient.

Either one of the peptide or the anti-TNF can be introduced into the patient, followed by the introduction of the other one.

In another aspect, the invention provides a vaccine against *Propionibacterium acnes*, including the above peptide and anti-TNF.

In another aspect, the invention provides a polynucleotide encoding the above peptide.

In another aspect, the invention provides an expression vector to which the above polynucleotide is operably linked. Use of the expression vector of the invention enables providing a peptide which can suppress inflammation caused by infection with *Propionibacterium acnes*.

In another aspect, the invention provides an antibody which specifically recognizes the above peptide.

In another aspect, the invention provides a method for determining effectiveness of a vaccine against *Propionibacterium acnes*. The method includes the step of detecting whether a polynucleotide encoding the above peptide exists in a sample gathered from a living body. Use of the method of the invention enables ease of determining whether the vaccine against *Propionibacterium acnes* is effective in a living body or not, before administering the vaccine to the living body.

In another aspect, the invention provides a method for treating or preventing inflammation caused by *Propionibacterium acnes* includes the step of administering to an individual the above vaccine, the vaccine containing a therapeutically effective amount of the peptide and anti-TNF.

In another aspect, the invention provides a method for treating or preventing inflammation caused by *Propionibacterium acnes* including the step of administering to an individual the above vaccine, the vaccine containing a therapeutically effective amount of the polynucleotide and anti-TNF.

BRIEF DESCRIPTION OF DRAWINGS

A further understanding of the invention can be gained from the following description of the preferred embodiments when read in conjunction with the accompanying drawings in which:

FIG. 6 is a diagram comparing a 16S rDNA base sequence of a strain isolated from a patient and a 16S rDNA base sequence of a standard strain;

SEQUENCE LISTING

Figure 1:
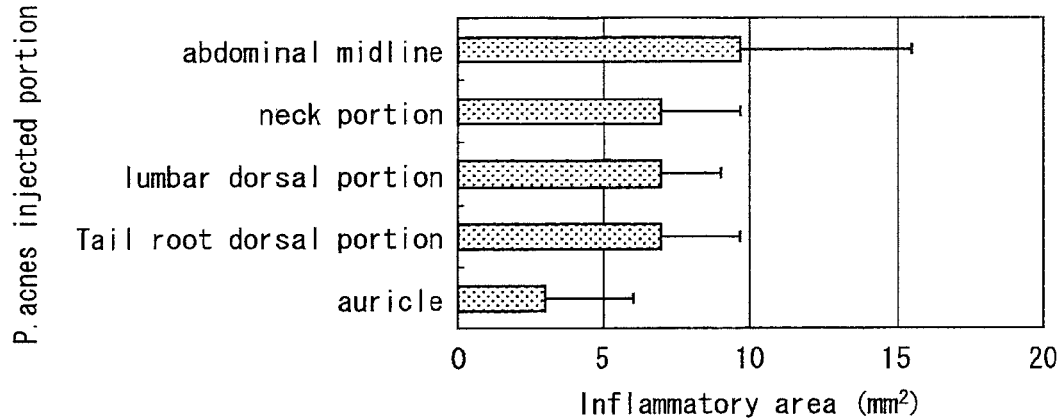
FIG. 1 is a diagram showing a result of measuring inflammatory areas caused by injection of *Propionibacterium acnes* into individual portions.

The amino acid sequences listed in the accompanying sequence listing are shown using standard letter abbreviations and the sequence listing is incorporated by reference herein.

DETAILED DESCRIPTION OF THE INVENTION

The invention provides compositions, methods and therapies to address *Propionibacterium acnes* in a patient and the inflammation resulting therefrom. The compositions, methods and therapies include the use of antigen peptide. In certain embodiments, the antigen peptide is administered in combination with anti-TNF. The antigen peptide with or without the presence of anti-TNF, is capable of inducing an immune response against *Propionibacterium acnes* infection and reducing or preventing inflammation caused by *Propionibacterium acnes*. The antigen peptide of the invention has a very high antigenicity. Therefore, use of the peptide with or without anti-TNF can provide a vaccine against *Propionibacterium acnes*.

In certain embodiments, use of peptide in combination with anti-TNF can produce enhanced or improved results relative to reducing or eliminating the inflammation resulting from *Propionibacterium acnes*. The anti-TNF for use in accordance with the invention can be in various forms. For example, the anti-TNF can be incorporated into a delivery mechanism, such as a liquid carrier or medium, to facilitate introduction such as, by injection.

The anti-TNF for use in accordance with the invention may include a wide variety of suitable materials. Non-limiting examples include any material which demonstrates an anti-TNF effect or result, e.g., reduces inflammation generated by TNF. Further, suitable anti-TNF materials for use in accordance with the invention can be selected from a wide variety of anti-TNF materials known in the art. In certain embodiments, a TNF inhibitor including a fusion protein, such as but not limited to, Entanercept may be used. Entanercept is commercially available under the trade name Enbrel.

The peptide for use in accordance with the invention may be one or more of peptides (a) to (d) as follows:

(a) a peptide consisting of an amino acid sequence indicated by SEQ NO. 1;

(b) a peptide consisting of an amino acid sequence derived from the amino acid sequence indicated by SEQ NO. 1 by deletion, substitution, insertion, or addition of one or several amino acids, the peptide generating, by immune response, an antibody suppressing an increase of *Propionibacterium acnes*;

(c) a peptide consisting of an amino acid sequence indicated by SEQ NO. 3; and (d) a peptide consisting of an amino acid sequence derived from the amino acid sequence indicated by SEQ NO. 3 by deletion, substitution, insertion, or addition of one or several amino acids, the peptide generating, by immune response, an antibody suppressing an increase of *Propionibacterium acnes*.

Here, the "several amino acids" can be, for example, two or three amino acids, and more preferably, two amino acids.

In an embodiment wherein an amino acid is substituted, preferable substitution is substitution of one amino acid for another amino acid that has the same properties as the one amino acid, such as substitution of one amino acid for another amino acid that has the same side-chain functional group as the one amino acid (e.g., substitution of Arg for Lys and substitution of Asp for Glu); and substitution of one hydrophobic amino acid for another hydrophobic amino acid (e.g., substitution of Val for Ile).

As used herein and the claims, the term "peptide" is used in a manner exchangeable with "polypeptide" or "protein".

The peptide consisting of the amino acid sequence indicated by SEQ NO. 1 corresponds to amino acid residues from 90th amino acid residue to 103rd amino acid residue in a membrane protein of *Propionibacterium acnes* which consists of an amino acid sequence registered in Genbank/EMBL/DDBJ with the Accession No. AAT84059. The peptide consisting of the amino acid sequence indicated by SEQ NO. 3 corresponds to amino acid residues from 260th amino acid residue to 272nd amino acid residue in a membrane protein of *Propionibacterium acnes* which consists of an amino acid sequence registered in Genbank/EMBL/DDBJ with the Accession No. YP_056445.

In general, in the production of antibodies, an amino acid sequence which is excellent as an antigen is a hydrophilic amino acid sequence and an amino acid sequence having abundant charges, and also an amino acid sequence that is predicted to have a turn structure. The charges may be either positive or negative and it is desirable to include at least five charged amino acids. Further, the length of a selected amino acid preferably corresponds to 10 to 15 residues. The amino acid sequence indicated by SEQ NO. 1 or 3 is selected accordingly.

These peptides induce immunity to *Propionibacterium acnes* that is xenobiotic. It is inferred that at the induction of immunity, production of specific antibody is induced as a result of induction of Th2 dominated immunity.

Methods of producing peptides in accordance with the invention can employ chemical synthesis or an expression vector. In the embodiments which employ chemical synthesis, the peptide of the invention can be produced by well-known methods of synthesis. Non-limiting examples include but are not limited to liquid peptide synthesis and solid phase peptide synthesis. In the embodiments which employ an expression vector, peptide may be produced from a transformant to which an expression vector has been introduced or may be produced using an in vitro translation system. For example, a polynucleotide encoding the peptide (e.g,. polynucleotide including a base sequence indicated by SEQ NO. 2 or 4) is inserted into an expression vector and the expression vector is introduced into a host cell. A target peptide can be produced in the host cell. The term "transformant" used herein and the claims indicates not only a cell, a tissue, and an organ, but also a living organism itself Methods for preparing a transformant include procedures that are well known in this field, such as transformation by introducing a recombinant vector into a host. Non-limiting examples of living organisms to be transformed include, but are not limited to, microorganisms, plants, and animals. Introduction of a gene into a host cell may be confirmed by a variety of procedures well known in this field, such as but not limited to PCR, Southern hybridization and Northern hybridization.

In the embodiments wherein the peptide of the invention is produced by preparing a transformant, it is preferable that the peptide is expressed stably in a host cell. However, the peptide may be expressed transiently in a host cell. The peptide thus produced may be purified by a known method. Non-limiting examples of suitable methods for purifying the peptide include, but are not limited to, gel filtration chromatography, ion exchange chromatography, and affinity chromatography.

In another aspect, the peptide of the invention may be in the form of a multivalent antigen peptide (which may be also referred to as MAP: Multiple Antigen Peptide) obtained by binding a plurality of peptides (a) or (b) or by binding a plurality of peptides (c) or (d) below via a linker, as follows:

(a) a peptide consisting of an amino acid sequence indicated by SEQ NO. 1;

(b) a peptide consisting of an amino acid sequence derived from the amino acid sequence indicated by SEQ NO. 1 by deletion, substitution, insertion, or addition of one or several amino acids, the peptide generating, by immune response, an antibody suppressing an increase of *Propionibacterium acnes;*

(c) a peptide consisting of an amino acid sequence indicated by SEQ NO. 3; and (d) a peptide consisting of an amino acid sequence derived from the amino acid sequence indicated by SEQ NO. 3 by deletion, substitution, insertion, or addition of one or several amino acids, the peptide generating, by immune response, an antibody suppressing an increase of *Propionibacterium acnes.*

MAP is a peptide capable of showing a higher antigenicity and is a multivalent peptide obtained by adding a linker to a C-terminus of a specific peptide, and binding via the linker the specific peptide with a MAP structure (matrix) constructed based on Lys. MAP may be synthesized by conventional and known methods. The number of specific peptides to be included in one MAP molecule is not particularly limited, but is preferably five or more. The upper limit of the number of specific peptides to be included in one MAP molecule is not limited since the number is preferably large in terms of antigenicity. In certain embodiments, restriction may be due to synthesis technique and therefore, MAP may be produced with the number of specific peptides being fifteen molecules or less.

In general, a Cys residue is used as an amino acid constituting a linker to be added to a specific peptide. However, in the peptide in the form of MAP in accordance with certain embodiments of the invention, there is used a linker including a Gly residue between a specific peptide and a Cys residue. Specifically, -GlyCys or -GlyGlyCys is added as a linker to a C-terminus of the specific peptide. For example, -GlyCys is added to a C-terminus of a peptide consisting of the amino acid sequence indicated by SEQ NO. 1, and -GlyGlyCys is added to a C-terminus of a peptide consisting of the amino acid sequence indicated by SEQ NO. 3. Since the Gly residue is added between the Cys residue and the C-terminus of the specific peptide, the Cys residue is given flexibility in rotation so that when binding to the MAP structure, the specific peptide does not suffer steric hindrance and the Cys residue at the linker can form an angle which enables the Cys residue to be close to a MAP reactive group. The linker for the peptide of the invention in the form of MAP is not limited by this linker, and may be a general linker constituted by the Cys residue.

In another aspect, the peptide of the invention is provided in the form of a peptide composition containing peptide (e) or (f), as follows:

(e) a peptide in the form of a multivalent antigen peptide obtained by binding a plurality of the peptides (a) or (b) via a linker; and (f) a peptide in the form of a multivalent antigen peptide obtained by binding a plurality of the peptides (c) or (d) via a linker.

The term "peptide composition" used herein and the claims indicates a substance containing a plurality of peptide components.

Individual peptide components can be combined in various ratios to form the peptide composition. The ratios of individual components is not particularly limiting and may be 1:1 (weight ratio), for example. Further, to ensure higher immunogenicity, the peptide composition preferably includes a peptide in the form of a multivalent antigen peptide obtained by binding via a linker a plurality of peptides consisting of the amino acid sequence indicated by SEQ NO. 1, and a peptide in the form of a multivalent antigen peptide obtained by binding via a linker a plurality of peptides consisting of the amino acid sequence indicated by SEQ NO. 3.

Further, the invention provides a polynucleotide encoding the peptides (a)-(d). Non-limiting examples of the polynucleotide of the invention include, but not limited to, a polynucleotide consisting of a base sequence indicated by SEQ NO. 2 or 4. The term "base sequence" as used herein is exchangeable with "nucleic acid sequence" or "nucleotide sequence", and is indicated as a sequence of deoxyribonucleotides (abbreviated as A, G, C, and T). The base sequence indicated by SEQ NO. 2 encodes the peptide consisting of the amino acid sequence indicated by SEQ NO. 1, and the base sequence indicated by SEQ NO. 4 encodes the peptide consisting of the amino acid sequence indicated by SEQ NO. 3.

The polynucleotide of the invention may be in the form of DNA or RNA. A person skilled in the art can easily produce the polynucleotide of the invention based on amino acid sequence information of the peptide of the invention and base sequence information encoding the peptide. Specifically, the polynucleotide of the invention can be produced by general DNA synthesis or PCR.

Further, the invention provides a vector containing the polynucleotide encoding the peptide. When the vector is used in production of the peptide, it is preferable that the vector is an expression vector to which the polynucleotide is operably linked. The phrase "operably linked to" as used herein and the claims indicates that a polynucleotide for encoding a target peptide is under the control of a control region such as a promoter and is capable of expressing the peptide in a host cell. A procedure for causing a polynucleotide encoding a target peptide to be "operably linked to" an expression vector so as to construct a desired vector is well known in the art. Further, the technique of introducing an expression vector into a host cell is also well known in the art. Accordingly, a person skilled in the art can easily produce a desired peptide in a host cell.

Use of the peptide of the invention and/or the polynucleotide of the invention enables inducing immunity to *Propionibacterium acnes*. Further, the peptide and/or polynucleotide of the invention in combination with anti-TNF enables inducing immunity to *Propionibacterium acnes*. That is, the peptide and/or peptide/anti-TNF combination of the invention and/or, the polynucleotide and/or polynucleotide/anti-TNF combination of the invention can serve as vaccines against *Propionibacterium acnes*. Accordingly, use of the peptide and/or peptide/anti-TNF combination of the invention and/or the polynucleotide and/or polynucleotide/anti-TNF combination of the invention enables subduing intradermic inflammation (e.g., acne and pimples) due to *Propionibacterium acnes*.

The invention also includes a vaccine against *Propionibacterium acnes* and contains the aforementioned peptide and/or peptide/anti-TNF combination, the aforementioned peptide composition and/or peptide composition/anti-TNF combination, or the aforementioned polynucleotide and/or polynucleotide/anti-TNF combination as an effective component. The term "vaccine" used herein indicates a vaccine which is used for immunotherapy (vaccine therapy) and which induces an immune response specific to the peptide of the invention.

The vaccine of the invention may be provided in the form of a vaccine composition or in the form of a vaccine kit. Herein, "a vaccine composition containing an effective component" and "a vaccine kit containing an effective component" are generically referred to as "a vaccine containing an effective component". "Kit" indicates a form in which individual components are contained in different substances such that at least one component is contained in one substance and the rest is contained in another substance. The vaccine composition and the vaccine kit will be detailed later herein.

In general, the term "vaccine composition" indicates "a vaccine substance in which two or more components exist as a whole so that the components are considered as one substance". Administration of the vaccine of the invention may be, for example, single administration of peptide or peptide and anti-TNF wherein the peptide consists of the amino acid sequence indicated by SEQ NO. 1 or the amino acid sequence indicated by SEQ NO. 3, or a mixture of these two peptides. In the embodiments wherein a mixture of two peptides is employed, even if an amino acid sequence of an antigen protein of *Propionibacterium acnes* which antigen protein corresponds to one of the two peptides is mutated and the anti-inflammatory effect of the one peptide is lost, the other peptide can exert the anti-inflammatory effect. Such a composition may contain other components (e.g., support which is pharmaceutically acceptable) in addition to the peptides and anti-TNF.

In general, when the peptide, anti-TNF and any other components are not combined into the vaccine composition, a combination of individual components cannot be recognized as one composition, but can be encompassed by the term "kit" and can be provided as a kit. This is readily understood by a person having ordinary skill in the art.

In certain embodiments, the invention provides a vaccine composition including the peptide of the invention and/or peptide and anti-TNF. In other embodiments, the vaccine composition contains the polynucleotide of the invention and/or polynucleotide and anti-TNF. The polynucleotide is preferably in a form capable of expressing the peptide encoded by the polynucleotide of the invention, and is more preferably provided in a form of an expression vector to which the polynucleotide of the invention is operably linked. As described above, the peptide of the invention or the polynucleotide of the invention is used as an effective vaccine component in preparing a vaccine against *Propionibacterium acnes*.

The vaccine of the invention can be used as a prophylactic vaccine or a therapeutic vaccine against *Propionibacterium acnes*. The term "prophylactic vaccine" as used herein and the claims indicates a vaccine administered to an un-infected and untreated individual to prevent the individual from being infected with a disease. The term "therapeutic vaccine" as used herein and the claims indicates a vaccine administered to an individual already infected with a disease to improve the infection or make the infection as small as possible or to eliminate the immunopathological effect of the disease.

Various conventional methods for preparing vaccines containing an effective component is well known by a person skilled in the art and may be employed to prepare the vaccines in accordance with the invention. The vaccines may be prepared in the form of a solution or a suspension such that they are injectable into the patient. Alternatively, the vaccine of the invention may be prepared in an appropriate solid form to be solved or suspended in a solution prior to injection into the patient. Such preparation may be emulsified or may be protein emulsified in a ribosome.

The effective component(s) of the vaccine composition of the invention may be mixed with a diluent which is pharmaceutically acceptable and is compatible with the effective component(s). Preferable examples of the diluent include water, physiological saline, dextrose, glycerol, ethanol, and mixtures thereof. Further, if desired, the vaccine composition of the invention may include a little amount of an assisting substance such as a wetting agent or emulsifier and pH buffer.

The vaccine composition of the invention may be administered by injection (including intradeunic one, hypodermic one, and intramuscular one) via various routes (e.g. nasal cavity, mucosa, oral, intravaginal, urethra, and intraocular) or may be non-orally administered using a patch (endermic administration) or a suppository or the like.

The vaccine composition of the invention may be administered orally. For oral administration, the vaccine composition of the invention is used in combination with a diluent such as pharmaceutical-grade mannitol, lactose, starch, magnesium stearate, sodium saccharate, cellulose, and magnesium carbonate. The vaccine composition of the invention when administered orally may be in the form of a solution, a suspension, a tablet, a pill, a capsule, a sustained release formulation, or a powder medicine. In embodiments wherein the vaccine composition of the invention is provided in a freeze-dried form, the freeze-dried substance may be reconstructed as a suspension before administration. The reconstruction is preferably carried out in a buffer solution.

The vaccine composition of the invention may contain an adjuvant for enhancing effectiveness of the vaccine. Examples of the effective adjuvant include, but not limited to, aluminum hydroxide, aluminum phosphate, aluminum potassium sulfate (alum), beryllium sulfate, silica, kaoline, carbon, water-in-oil type emulsion, oil-in-water type emulsion, Muramyl dipeptide, bacterial endotoxin, fat X, Bordetella pertussis, Corynebacterium parvum, polyribonucleotide, sodium alginate, lanoline, lysolecithin, vitamin A, sponin, liposome, levamisole, DEAE-dextran, block copolymer, and other synthesized adjuvant. These adjuvants are commercially available from various suppliers. Representative examples of these adjuvants include an oil-in-water type adjuvant, an aluminum hydroxide adjuvant, and an adjuvant mixed with these adjuvants. An adjuvant which is permitted to be applied to humans is aluminum hydroxide.

In another aspect, the invention provides a vaccine kit. The vaccine kit corresponds to the aforementioned vaccine composition, and may include the peptide of the invention or the polynucleotide of the invention as an effective vaccine component and may include anti-TNF, and may further include one or more optional components.

In certain embodiments, the vaccine kit of the invention includes the peptide of the invention and/or peptide and anti-TNF. In another embodiment, the vaccine kit of the invention contains the polynucleotide of the invention and/or polynucleotide and anti-TNF. The polynucleotide of the invention is preferably in a form capable of expressing the peptide encoded by the polynucleotide of the invention, and is more preferably provided in a form of an expression vector to which the polynucleotide of the invention is operably linked.

The kit typically includes a package with one or more containers (e.g., bottle, plate, tube, and dish) having therein a specific material. The kit preferably has directions for using the individual materials contained in any one of individual containers constituting the kit. Further, the kit of the invention may be a package in which a plurality of different compositions are contained. The form of the composition may be as above, and if the composition is in the form of a solution, the composition may be contained in a container. The kit of the invention may be designed such that materials A and B are mixed and included in a single container or are included in respective containers. The "directions" may be written on a paper or other kind of a medium or may be printed out. Alternatively, the "directions" may be in the form of a magnetic tape or an electronic medium such as a computer-readable disc or tape and a CD-ROM. Further, the kit of the invention may include a container containing a diluent, a solvent, a cleaning liquid, or other reagent. Further, the kit may include beforehand an instrument necessary for prevention/treatment of acne caused by infection with *Propionibacterium acnes*.

Use of the vaccine of the invention as above enables efficiently preventing/treating inflammation (acne) caused by infection with *Propionibacterium acnes*.

That is, a method for treating or preventing inflammation caused by *Propionibacterium acnes*, including the step of administering to an individual a vaccine containing a therapeutically effective amount of the peptide of the invention or a therapeutically effective amount of the polynucleotide of the invention, and optionally a therapeutically effective amount of anti-TNF.

The term "therapeutically effective amount" used herein indicates the amount of peptide or polynucleotide which amount enables the peptide or the polynucleotide to exert a desired therapeutic effect or prophylactic effect. In embodiments, wherein anti-TNF is present, the anti-TNF may also be present in a therapeutically effective amount. The therapeutically effective amount may differ depending on the age, the weight, and other health conditions of an individual to which the vaccine is administered, on the condition of an inflammation to be treated, and on a method of administration. In all instances, at its most basic level, the desired effect is a regression, reduction or elimination of tumor cells in tumor tissue of the patient when compared to the tumor cells in the tumor tissue of the patient prior to employing the therapy methods of the invention. In certain embodiments of subcutaneous administration, administration of a vaccine may be such that 5-10 μg of the peptide per kg weight or 10-50 μg of the polynucleotide per kg weight is supplied in one administration. To induce an immune response sufficient for anti-inflammation, the vaccine may be administered multiple times, two times or more, to the patient. In certain embodiments, administration is made at a predetermined interval.

Another example is as follows: in a case of a vaccine including a mixture of MAP based on the peptide consisting of the amino acid sequence indicated by SEQ NO. 1 and MAP based on the peptide consisting of the amino acid sequence indicated by SEQ NO. 3 (weight ratio is 1:1), administration may be made via hypodermic injection in such a manner that 100-500 μg of each peptide per one shot is administered in the form of a physiological saline solution five times or so at an interval of from three to five days.

In a case of administration via a patch, one dose may be small, the number of dose may be reduced, and an individual can treat himself/herself using the patch.

The term "patient or individual" used herein indicates individual humans and mammals other than humans (such as rats, mice, rabbits, pigs, cattle, and monkeys).

The invention provides an antibody which specifically recognizes any of the peptides of the invention. That is, an antibody of the invention can specifically bind to any of the peptides. In certain embodiments, the antibody is preferably an antibody which binds to (1) the peptide consisting of the amino acid sequence indicated by SEQ NO. 1 or 3 or (2) a multivalent antigen peptide synthesized by the MAP process from the peptide consisting of the amino acid sequence indicated by SEQ NO. 1 or 3.

The term "antibody" used herein indicates an immunoglobulin (IgA, IgD, IgE, IgG, IgM, and Fab fragments thereof, F(ab')$_2$ fragment and Fc fragment). Examples of the antibody include, but not limited to, polyclonal antibodies, monoclonal antibodies, single-chain antibodies, and antiidiotype antibodies.

The antibody of the invention may be produced by conventional methods known in the field to which the invention pertains. For example, the antibody can be obtained by administering the peptide of the invention to a living body of a mammal and causing an immune response so that an antibody is produced in the living body. The antibody obtained in this case is generally a polyclonal antibody. A monoclonal antibody can be produced by conventional and known hybridoma techniques using the peptide of the invention. Alternatively, the monoclonal antibody can be produced by application of a recombinant DNA technique or chemical synthesis.

Use of the antibody of the invention enables one to easily purify the peptide of the invention. For example, by subjecting the peptide of the invention expressed in a cell using the vector of the invention or the transformant of the invention to affinity purification using the antibody of the invention, it is possible to efficiently collect the peptide.

The antibody of the invention may be any antibody provided the antibody specifically binds to the peptide of the invention. The antibody is not limited in terms of the kinds of individual immunoglobins (IgA, IgD, IgE, IgG, or IgM), a method for preparing a chimeric antibody, a method for preparing a peptide antigen and the like, which are specifically described herein. Therefore, an antibody obtained by a method other than the above-described methods is also encompassed in the invention.

A method of the invention for determining effectiveness of a vaccine against *Propionibacterium acnes* is only required to include a detection step of detecting whether a polynucleotide encoding the above peptide exists or not in a sample collected from a living body, and is not particularly limited in terms of other specific steps and instruments and devices to be used.

In a case where a polynucleotide encoding the peptide is detected in the detection step, it can be determined that administration of the vaccine of the invention to a test subject is highly likely to result in efficient suppression of inflammation caused by *Propionibacterium acnes*. Specifically, when the polynucleotide encoding the above peptide is detected, it is determined that the vaccine of the invention is likely to be effective against *Propionibacterium acnes*.

The method for detecting the polynucleotide encoding the peptide is not particularly limited. For example, the method may be detection by PCR amplification or detection by determining a base sequence of a PCR product. By determining the base sequence of the PCR product, it is possible to determine more accurately whether a vaccination effect can be exerted or not. Whether the vaccination effect can be exerted or not may be determined also depending on whether a PCR fragment is generated or not by amplification. For example, in a case where a fragment with a desired length is generated by amplification. using a specific primer for amplifying the above polynucleotide (in a case where the result of PCR detection is positive), it is highly possible that the test subject is infected with *Propionibacterium acnes* retaining the above polynucleotide, and so it is determined that the vaccination effect is highly expected. On the other hand, in a case where a fragment with a desired length is not generated (in a case where the result of PCR detection is negative), it is determined that the vaccination effect is expected little. Before PCR amplification, *Propionibacterium acnes* that can be contained in a sample collected from the test subject may be grown by culturing the sample.

A method for determining whether the vaccine of the invention against *Propionibacterium acnes* is to be used or not may be made by detecting whether a partial sequence of 16S rDNA of *Propionibacterium acnes* in a sample collected from a living body exists or not. Detection of whether the partial sequence of 16S rDNA exists or not may be detection by PCR amplification and detection by determining a base sequence of a PCR product. This determination may indicate that the inflammation of the test subject is derived from *Propionibacterium acnes*. This may be a basis for using the vaccine.

A model animal which is a mammal other than humans, such as mice in later-mentioned Examples, whose abdominal midline was intradermically injected with *Propionibacterium acnes* with predetermined bacterial cell concentration or more to cause inflammation of *Propionibacterium acnes*, and a method for preparing the model animal, are also encompassed in the invention. In the model animal, inflammation of *Propionibacterium acnes* is created in a more efficient manner than a conventional method for creating inflammation. A determination system having been used so far in developing an anti-acne drug is a one based on the assumption that the drug is applied. Consequently, in developing a vaccine, there has been constructed so far no assured determination system which can determine the effect of the vaccine in vivo. The method for determining effectiveness of the vaccine, the model animal, and the method for preparing the model animal can be preferably used in developing a vaccine against *Propionibacterium acnes*.

The following explains embodiments of the invention in more detail, with reference to Examples. It should be noted that the invention is not limited to the Examples below and may be modified in terms of its details. The invention is not limited to the description of the embodiments above, but may be altered by a skilled person within the scope of the claims. An embodiment based on a proper combination of technical means disclosed in different embodiments is encompassed in the technical scope of the invention. All the documents cited in the specification are incorporated by reference.

EXAMPLES

Example 1

Culture of *Propionibacterium Acnes*

Strains of *Propionibacterium acnes* (hereinafter abbreviated as "*P. acnes*") (ATCC6919) were purchased from RIKEN BioResource Center (JCM Catalogue No. 6425). The strains of the purchased *P. acnes* were cultured according to culture condition information from the center. Specifically, in an anaerobic glove box, the strains of the *P. acnes* were suspended in 100 ml of a GAM culture medium (manufactured by Nippon Suisan Kaisha, Ltd.) and cultured anaerobically using a vial at 37° C. for three days.

Example 2

Causing Intradermical Inflammation in Mouse Skin by *P. Acnes*

Living bacterial cells of *P. acnes* were put in a deaerated physiological saline while keeping an anaerobic condition to prepare a suspension with the number of the living bacterial cells of *P. acnes* of $5 \times 10^7$ cells/ml, $1 \times 10^8$ cells/ml, or $5 \times 10^8$ cells/ml. The anaerobic condition was kept by spraying a nitrogen gas. The number of the living bacterial cells of *P. acnes* was calculated based on the assumption that OD measurement value of 0.98-1.02 at 550 nm measured by a spectrophotometer corresponds to $5 \times 10^8$ cells/ml, with reference to Ramstad S. et al., Photochem. Photobiol. Sci., 2006, 5, 66-72.

50 µl of the prepared suspension of *P. acnes* was intradennically injected into shaven abdominal midlines, neck portions, lumbar dorsal portions, tail root dorsal portions, and auricles of male Balb/c mice (9-10 weeks old). The inflammatory areas (major axis x minor axis: $mm^2$) at individual portions to which the suspension was injected intradermically were measured at predetermined times. Each group consisted of five individuals.

Figure 2:
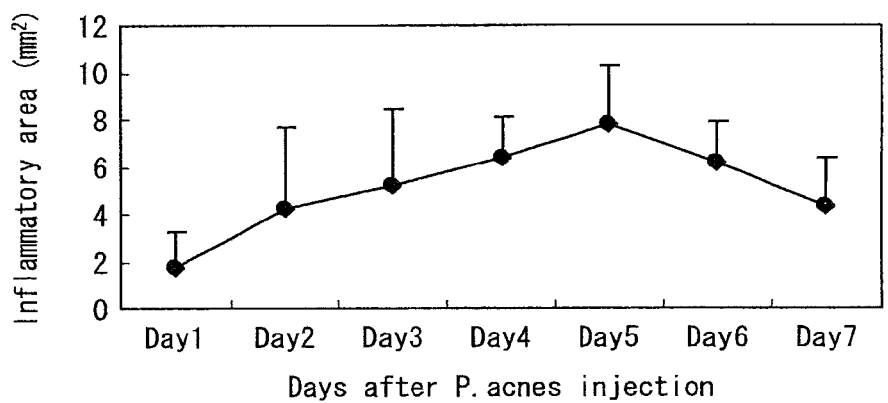
FIG. 2 is a diagram showing a relation between an inflammatory area caused by injection of *Propionibacterium acnes* and elapsed time after the injection.

As a result, in a group to which the suspension of *P. acnes* whose bacterial cell concentration was $5 \times 10^8$ cells/ml was injected, inflammation was apparently confirmed. FIG. 1 is a graph showing the result of inflammatory areas at individual portions observed five days after the injection. As illustrated in FIG. 1, inflammation was observed in individual portions to which the suspension was intradermically injected, and the inflammatory area was largest at an intradermic portion of the abdominal midline. That is, when causing intradermic inflammation of mice, intradermic injection into the abdominal midline was most effective. Inflammation at the auricle was the mildest among the observed portions. FIG. 2 is a graph showing the result of the inflammatory area at the abdominal midline at individual times after the suspension was intradermically injected into of the abdominal midline. As illustrated in FIG. 2, the inflammatory area at the abdominal midline was largest five days after the injection of *P. acnes*.

In contrast thereto, in the groups to which the suspensions of *P. acnes* whose bacterial cell concentrations were $5 \times 10^7$ cells/ml and $1 \times 10^8$ cells/ml, respectively, were injected, no inflammation could be caused at any portions and at any times.

Example 3

Preparation of Peptide

The powder of PepA which was a peptide consisting of the amino acid sequence indicated by SEQ NO. 1 or the powder of PepD which was a peptide consisting of the amino acid sequence indicated by SEQ NO. 3 was dissolved in physiological saline (produced by Otsuka Pharmaceutical Co., Ltd.) to prepare 800 µg/ml of a peptide solution.

As Comparative Examples, there were used PepB which was a peptide corresponding to 10th-26th amino acid residues in a membrane protein of *Propionibacterium acnes* which consists of the amino acid sequence registered in Genbank/EMBL/DDBJ accession No. AAT81852, and PepC which was a peptide corresponding to 145th-166th amino acid residues in a membrane protein of *Propionibacterium acnes* which consists of the amino acid sequence registered in Genbank/EMBL/DDBJ accession No. YP_055518. Table 1 shows information on the amino acid sequence in individual peptides. The sequences used as the Comparative Examples were amino acid sequences which may be strong candidates for antigens in producing antibodies, i.e. amino acid sequences which are abundant in hydrophilic amino acids and charges, and were selected from amino acid sequences with a turn structure. Further, the proteins consisting of the amino acid sequences registered in the above accession Nos. are proteins supposed to be expressed as a result of genome analysis described in Bruggemann H. et al., "The Complete Genome Sequence of Propionibacterium Acnes, a Commensal of Human Skin," Science, 2004, 305, 671-673.

TABLE I

| Peptide Name | Amino Acid Sequence | SEQ No. | Accession No. Derived Protein |
|---|---|---|---|
| PepA | $^{90}$AIQEKYGDDRERAG$^{103}$ | 1 | AAT84059 |
| PepB | $^{10}$GRKPDTNKRSWHRKASR$^{26}$ | 11 | AAT81852 |
| PepC | $^{145}$IDQVREYRHRDDDDDEDPGEDG$^{166}$ | 12 | YP_055518 |
| PepD | $^{260}$KDADKDNPTYQKV$^{272}$ | 3 | YP_056445 |

Example 4

Anti-Inflammatory Effect of Peptide PepA Against Inflammation Caused by *P. Acnes*

Figure 3:
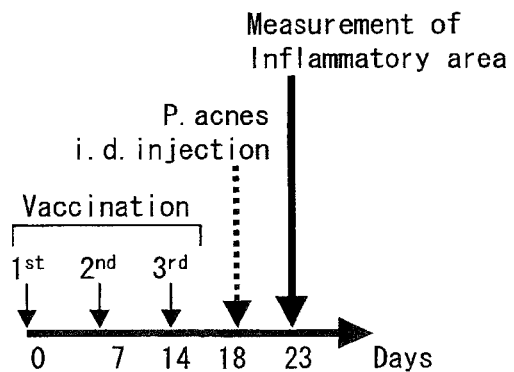
FIG. 3 is a diagram illustrating steps of examining anti-inflammatory effects of peptides.

In Example 2, the area of the inflammation caused by *P. acnes* was largest when five days had passed from intradermic injection of 50 µl of *P. acnes* ($5 \times 10^8$ cells/ml) into the abdominal midline. Accordingly, the anti-inflammatory effects of individual peptides were determined under the same conditions, i.e. by intradermically injecting 50 µl of *P. acnes* ($5 \times 10^8$ cells/ml) into the abdominal midline and measuring the inflammatory area ($mm^2$) five days after the injection. FIG. 3 illustrates the procedure for examining the anti-inflammatory effect.

FIG. 3 is a drawing schematically illustrating the procedure for examining the anti-inflammatory effect. As illustrated in FIG. 3, PepA (40 µg/50 µl/one individual) was intradermically vaccinated into dorsal portions of male Balb/c mice (7 weeks old at the first vaccination of PepA) 18 days before the injection of living bacterial cells of *P. acnes* (Day "0" in FIG. 3), 11 days before the injection (Day "7" in FIG. 3), and 4 days before the injection (Day "14" in FIG. 3), i.e. three times in total. Then, *P. acnes* was intradermically injected into the abdominal midlines of the mice, and the inflammatory areas were measured 5 days after the injection (Day "23" in FIG. 3). Each group consisted of 10 mice. As Comparative Examples, there were prepared a group of mice to which PBS without PepA was administered and a group of mice to which PepB or PepC was administered instead of PepA, and *P. acnes* was injected into the groups similarly. These results are shown in FIG. 4.

Figure 4:
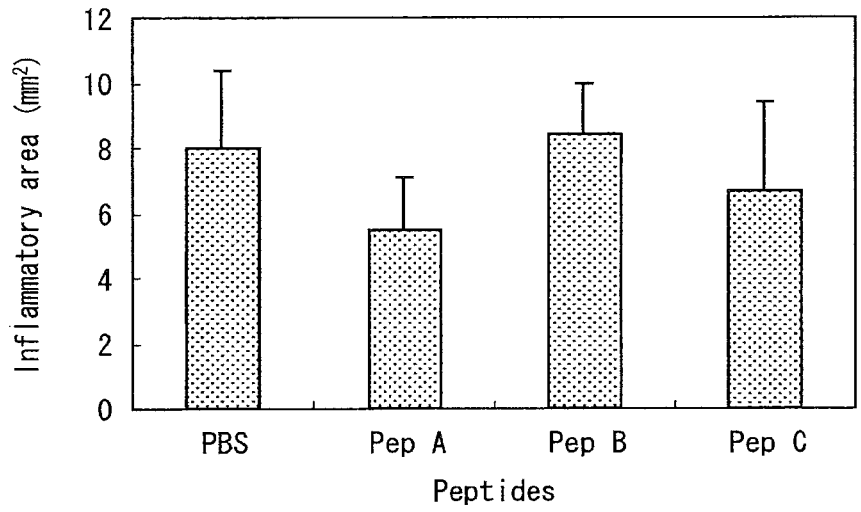
FIG. 4 is a diagram showing a result of examining anti-inflammatory effects of peptides.

FIG. 4 is a graph showing the result of the anti-inflammatory effect of PepA. As illustrated in FIG. 4, the group to which PepA was administered exhibited a statistically significantly reduced inflammatory area (P=0.00865 (P<0.01)), compared with the control group to which PBS was administered. That is, PepA statistically significantly exhibits the anti-inflammatory effect against the inflammation caused by *P. acnes*. In the case of the group to which PepB was administered, P=1. In the case of the group to which PepC was administered, P=0.1655. These numerals were not significant statistically, and so it was considered that PepB and PepC do not exhibit the anti-inflammatory effect against the inflammation caused by *P. acnes*.

The above results show that the composition containing the peptide PepA is effective as a vaccine against *P. acnes*, i.e. an acne vaccine.

Example 5

Anti-Inflammatory Effect of Peptides PepA and PepD Against Inflammation Caused by *P. Acnes*

The anti-inflammatory effects of individual peptides were examined using an inflammation causing system under the same conditions as in Example 4 except that the peptides to be administered to mice before injection of *P. acnes* were changed from PepA, PepB, and PepC to PepA and PepD. The results are shown in FIG. 5.

Figure 5:
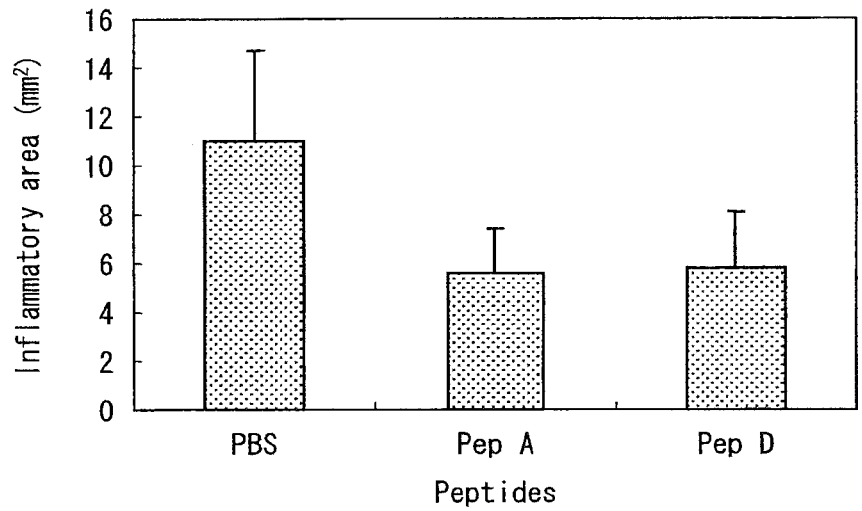
FIG. 5 is a diagram showing another result of examining anti-inflammatory effects of peptides.

FIG. 5 is a graph showing the results of the anti-inflammatory effects of PepA and PepD. As shown in FIG. 5, the group to which PepA was administered exhibited a statistically significantly reduced inflammatory area (P=0.0012 (P<0.01)), compared with the control group to which PBS was administered, as in the result of Example 4. Further, the group to which PepD was administered exhibited a statistically significantly reduced inflammatory area (P=0.00175 (P<0.01)), compared with the control group to which PBS was administered.

The above results show that the composition containing the peptide PepA or PepD is effective as a vaccine against *P. acnes*, i.e. an acne vaccine.

Example 6

Identification of Strain Harbored by Acne Patient Extraction of 16S rDNA

Purulence collected from a diseased part of an acne patient was cultured anaerobically on a GAM flat plate agar medium at 37° C., and a part of the bacterial cells was collected. The collected bacterial cells were transferred to a GAM flat plate agar medium and cultured anaerobically so that a single colony was produced. Bacterial cells from the single colony were collected, and suspended in a 20 mM NaOH aqueous solution. The suspension was heated at 94° C. for 3 min, the bacterial cells were lysed, and 16S rDNA was extracted. Using the extracted 16S rDNA, a base sequence of 16S rDNA of the bacterial cells with which the patient was infected was determined. The base sequence was determined with respect to each of three sets of bacterial cells collected from three acne patients, respectively.

Determination of Base Sequence of 16S rDNA

The extracted 16S rDNA was used as a template DNA. Further, as a primer, there were used primer 9F (forward primer): 5'-GTTTGATCCTGGCTCA-3' (SEQ NO. 5) and primer 800R (reverse primer): 5'-TACCAGGG-TATCTAATCC-3' (SEQ NO. 6). PCR carried out here consisted of 30 cycles each consisting of a step at 94° C. for 30 seconds, a step at 55° C. for 60 seconds, and a step at 72° C. for 60 seconds. The PCR was carried out by AmpliTaq Gold DNA Polymerase (manufactured by Applied Biosystems). After the reaction, a PCR product was purified. Subsequently, a cycle sequence reaction was carried out using the purified PCR product. A product obtained in the cycle sequence reaction was purified, supplied to an ABI PRISM 310 Genetic Analyzer System (manufactured by Applied Biosystems), and a base sequence was determined using analysis software BioEdit. The primers used in the cycle sequence reaction were the above primer 9F and primer 536R: 5'-GTATTACCGCGGCTGCTGG-3' (SEQ NO. 7). The cycle sequence reaction consisted of 25 cycles each consisting of a step at 96° C. for 10 seconds, a step at 50° C. for 5 seconds, and a step at 60° C. for 4 minutes.

Result of Determining Base Sequence

The result of determining the base sequence showed that in each of three separated bacterial strains that were established, derived from patients (patient strains 1-3), the base sequence of 16S rDNA at an amplified part (SEQ NO. 16) had the same sequence as that of the corresponding base sequence in ATCC6919 strain of *P. acnes* (SEQ NO. 8). FIG. 6 shows the result with respect to the patient strain 1. Accordingly, the three separated bacterial cells derived from the patients were identified as *P. acnes*.

Example 7

Anti-Inflammatory Effect of Peptide PepA Against Inflammation Caused by *P. Acnes* Derived from Patient The anti-inflammatory effect of PepA was examined by the same procedure as in Example 5 except that bacterial cells of *P. acnes* to be injected into mice were the acne-patient-derived bacterial cells of *P. acnes* which were isolated in Example 6. The result is shown in FIG. 7.

Figure 7:
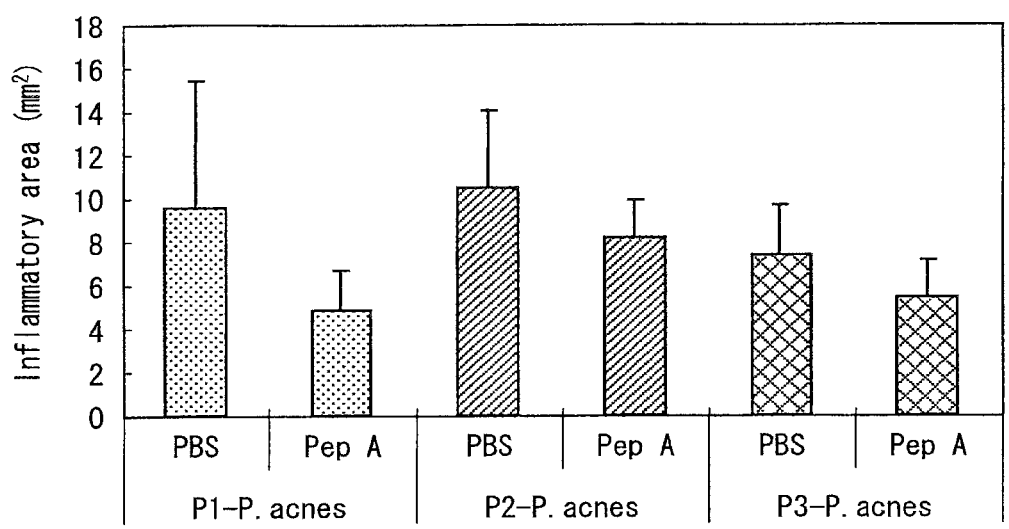
FIG. 7 is a diagram showing a result of examining anti-inflammatory effects of a peptide against injection of *Propionibacterium acnes* isolated from a patient.

FIG. 7 is a graph showing the result of intradermically injecting, after immunization by PepA, the patient strains 1-3 (P1-*P. acnes* to P3-*P. acnes*) to the abdominal midlines of mice and measuring inflammatory areas of the mice 5 days after the injection. As shown in FIG. 7, the group to which PepA was administered showed P=0.0252 (P<0.05) with respect to the patient strain 1, P=0.0476 (P<0.05) with respect to the patient strain 2, and P=0.0237 (P<0.05) with respect to the patient strain 3, compared with the control group to which PBS was administered instead of PepA. That is, administration of PepA enabled statistically significantly reducing an inflammatory area with respect to injection of each of the patient strains. This suggests that PepA is widely effective as an acne vaccine.

Example 8

Examination of Base Sequence Encoding PepA or PepD in *P. Acnes* Derived from Acne Patient In order that PepA or PepD serves effectively as a vaccine, it is desirable that target *P. acnes* strains have a protein containing PepA or PepD. Accordingly, whether the target *P. acnes* strains had a protein containing PepA or PepD was examined by carrying out PCR and by determining and checking a base sequence of PCR products.

Confirmation of PepA by PCR

Primers used here for detecting a base sequence encoding an amino acid sequence of PepA were primer L: 5'-GAT-GAAAGCCATCCAGGAAA-3' (SEQ NO. 9) and primer R: 5'-GCACACGAAACAACGCTAGA-3' (SEQ NO. 10). PCR carried out here consisted of 35 cycles each consisting of a step at 95° C. for 15 seconds, a step at 60° C. for 20 seconds, and a step at 72° C. for 30 seconds. The PCR was carried out using AmpliTaq Gold DNA Polymerase (manufactured by Applied Biosystems).

As a result, a PCR fragment with a desired length was obtained by amplification from the detected patient-derived *P. acnes*, and consequently existence of a base sequence encoding the amino acid sequence of PepA was deduced. This suggests that a protein corresponding to PepA has the same amino acid sequence as that of PepA.

Further, specimens collected from 21 volunteers were examined as to whether they had a base sequence encoding the amino acid sequence of PepA, and 19 cases out of 21 cases were positive. The term "positive" used in the present Examples indicates that a fragment with a desired length was generated by PCR amplification using a specific primer. The term "negative" used in the present Examples indicates that a fragment with a desired length could not be generated by PCR amplification using a specific primer.

Similarly, the specimens collected from the 21 volunteers were examined by PCR as to whether they had 16S rDNA of *P. acnes*. The result showed that the 19 cases being positive in examination of the base sequence encoding the amino acid sequence of PepA was also positive in examination of 16S rDNA, and the 2 cases being negative in examination of the base sequence encoding the amino acid sequence of PepA was also negative in examination of 16S rDNA. The results of the 2 cases being negative in PCR detection for confirming the base sequence encoding the amino acid sequence of PepA do not indicate that the base sequence encoding the amino acid sequence of PepA was not carried by the 2 volunteers but indicates that the number of bacterial cells of *P. acnes* was so low that the bacterial cells could not be detected. From the above results, it was suggested that a protein containing the amino acid sequence of PepA exists in the 19 cases in which 16S rDNA of *P. acnes* was confirmed.

TABLE 2

| Subjects | Total | Mean Age | Mongoloid | Caucasoid | PCR Positives (%) |
|---|---|---|---|---|---|
| Male | 4 | 25.75 | 2 | 2 | 4 (100) |
| Female | 15 | 29.43 | 14 | 1 | 15 (100) |
| Total | 19 | 28.61 | 16 | 3 | 19 (100) |
| PCR Positives (%) | 19 (100) | | 16 (100) | 3 (100) | |

Further, similarly as above, specimens collected from another 11 volunteers were examined by PCR as to whether they had 16S rDNA of *P. acnes*. The result showed that each of the specimens was *P. acnes* positive. Further, the 11 cases were examined as to whether they had a base sequence encoding the amino acid sequence of PepA and all of the 11 cases were found to be positive. Table 3 shows the results of the 11 cases together with the results of the 19 cases which were found to be positive.

TABLE 3

| Subjects | Total | Mean Age | Mongoloid | Caucasoid | PCR Positives (%) |
|---|---|---|---|---|---|
| Male | 7 | 25.86 | 5 | 2 | 7 (100) |
| Female | 23 | 29.55 | 22 | 1 | 23 (100) |
| Total | 30 | 28.66 | 27 | 3 | 30 (100) |
| PCR Positives (%) | 30 (100) | | 27 (100) | 3 (100) | 30 (100) |

Confirmation of Base Sequences Encoding PepA and PepD

With respect to each of specimens collected from 5 volunteers and *P. acnes* described in Example 1, DNA encoding the amino acid sequence of PepA and DNA encoding the amino acid sequence of PepD were amplified by PCR. In amplifying DNA encoding PepA, the primer L (SEQ NO. 9) and the primer R (SEQ NO. 10) were used as primers. In amplifying DNA encoding PepD, primer om1L: 5'-GGTGCTGTCGTCAATAACAACTTC-3' (SEQ NO. 14) and primer om1R: 5'-GGAGTGGCCAGAGACGATCT-3' (SEQ NO. 15) were used as primers. PCR carried out here consisted of (i) a step at 95° C. for 5 minutes, thereafter (ii) 35 cycles each consisting of a step at 95° C. for 15 seconds, a step at 53° C. for 20 seconds, and a step at 72° C. for 30 seconds, and thereafter (iii) a step at 72° C. for 7 minutes and a step at 25° C. for 10 minutes. Table 4 shows the result of PCR.

As shown in Table 4, in all the specimens, with respect to PepA, PCR products with a desired size were generated by amplification. The cases where the PCR products with a desired size were generated by amplification are shown as "positive". With respect to PepD, PCR products with a desired size were generated by amplification except for the specimen of the patient strain D.

Subsequently, base sequences of the PCR products were determined to determine deduced amino acid sequences. Determination of the base sequences was made by using 3130x1 Genetic Analyzer, Sequencing Analysis Software ver 5.3.1, and KB BaseCaller (each manufactured by Applied Biosystems). Table 4 shows the result. As shown in Table 4, in all the specimens, the sequence of PepA was conserved. That is, the deduced amino acid sequence thus obtained was the same as the amino acid sequence indicated by SEQ NO. 1. On the other hand, in the specimens of the patient strains C and E, the sequence of PepD was conserved. That is, the deduced amino acid sequence thus obtained was the same as the amino acid sequence indicated by SEQ NO. 3. In the specimens of the patient strains A and B, the deduced amino acid sequence had one mutation of amino acid. Specifically, an amino acid residue positioned 11.sup.th from N-terminus of the amino acid sequence indicated by SEQ NO. 3 was changed from Gln to Lys. This mutation was also observed in strains derived from Riken BioResource Center which were used to determine the anti-inflammatory effect of individual peptides in the Examples. The patient strain A is a specimen derived from the acne patient in the Example 6.

TABLE 4

| | PCR | | Amino Acid Sequence | |
|---|---|---|---|---|
| Specimen | PepA | PepD | PepA | PepD |
| Stain derived From Riken (JCM6425) | Positive | Positive | Sequence Conservation | Partial Mutation ($^{11}$Gln→Lys) |

TABLE 4-continued

| | PCR | | Amino Acid Sequence | |
|---|---|---|---|---|
| Specimen | PepA | PepD | PepA | PepD |
| Patient strain A | Positive | Positive | Sequence Conservation | Partial Mutation ($^{11}$Gln→Lys) |
| Patient strain B | Positive | Positive | Sequence Conservation | Partial Mutation ($^{11}$Gln→Lys) |
| Patient strain C | Positive | Positive | Sequence Conservation | Sequence Conservation |
| Patient strain D | Positive | Negative | Sequence Conservation | |
| Patient strain E | Positive | Positive | Sequence Conservation | Sequence Conservation |

However, as shown in the Example 5 and FIG. 5, single administration of PepD can yield an anti-inflammatory effect on inflammation caused by strains derived from RIKEN BioResource Center which contain mutation in the amino acid sequence of PepD. This shows that PepD can serve as a vaccine effectively even on inflammation caused by strains containing PepD having mutation of one amino acid.

Similarly, in *P. acnes* in the specimens collected from the 30 volunteers shown in Table 5, DNA encoding the amino acid sequence of PepA and DNA encoding the amino acid sequence of PepD were amplified by PCR and base sequences of respective PCR products were determined, so that respective deduced amino acid sequences were determined. Table 5 shows the results.

TABLE 5

| PCR Detection (Simple) | Number of Cases | Number of Cases of Complete Sequence Conservation | Number of Cases of Partial Sequence Mutation | Number of Cases of Unidentified Sequende |
|---|---|---|---|---|
| PepA Positive | 30 | 30 | 0 | 0 |
| PepA Negative | 0 | 0 | 0 | 0 |
| PepD Positive | 26 | 20 | 6 ($^{11}$Gln→Lys in all cases) | 0 |
| PepD Negative | 4 | 0 | 0 | 4 |

As shown in Table 5, in all the specimens examined here, the amino acid sequence of PepA was conserved completely. The results of Tables 4 and 5 show that the PepA sequence of actual patient-derived *P. acnes* was conserved very well.

On the other hand, in the 20 cases out of the 30 cases examined, the amino acid sequence of PepD was conserved completely (66.7%). In the 6 cases out of the cases examined, the amino acid sequence was partially mutated ($^{11}$Gln-→Lys). This is a partial mutation equal to that of the RIKEN BioResource Center strains to which administration of a vaccine was found to be effective by the test using mice. Accordingly, in view of the effectiveness of a vaccine effect, the PepD sequence is supposed to be effective in 26 cases out of the 30 cases (86.7%). That is, the PepD sequence was conserved well.

In view of the above, it is considered that PepA and PepD have sequences which are well conserved in bacterial cells of patients, and therefore are highly effective as vaccines for patients.

Example 9

Vaccine Use Against *P. Acnes*

Preparation of Vaccine

As described above, it was found in the acne inflammatory causing test system using mice in the Example 5 that two kinds of single chain peptides (PepA and PepD) have an anti-inflammatory effect. In order that these peptides work more effectively, MAP peptides for PepA and PepD were synthesized by the MAP process. The synthesis peptide thus obtained consisted of 7-13 molecules of the single chain peptide of PepA or PepD bound to a MAP structure. A MAP peptide mixture solution in which the MAP peptides for PepA and PepD, respectively, were mixed was prepared and used as a vaccine.

Preparation of the mixture solution was made as follows. Initially, individual MAP peptides were prepared, and then dialyzed with distilled water, and freeze-dried and powdered. Subsequently, respective powders were dissolved in physiological saline (produced by Otsuka Pharmaceutical Co., Ltd.) so that concentrations of the respective MAP peptides were 1 mg/ml (each of the resulting solutions are hereinafter referred to as "PA-MAP solution"). The PA-MAP solutions were subjected to an endotoxin examination and a cytotoxic examination. The amount of endotoxin met the allowable amount (5 EU or less/kg weight/1 shot) according to NIH. Further, in the cytotoxic examination, 10 µl of a test peptide solution and 90 µl of peripheral-blood mononuclear cells ($2×10^6$ cells/ml in plain RPMI 1640) were co-cultured at 37° C. for 24 hours. The cell survival ratio was substantially equal (with difference of +/−5% or less) to that of a control in which peripheral-blood mononuclear cells to which physiological saline was added were cultured, and consequently no toxicity was found.

Case 1

Figure 8:
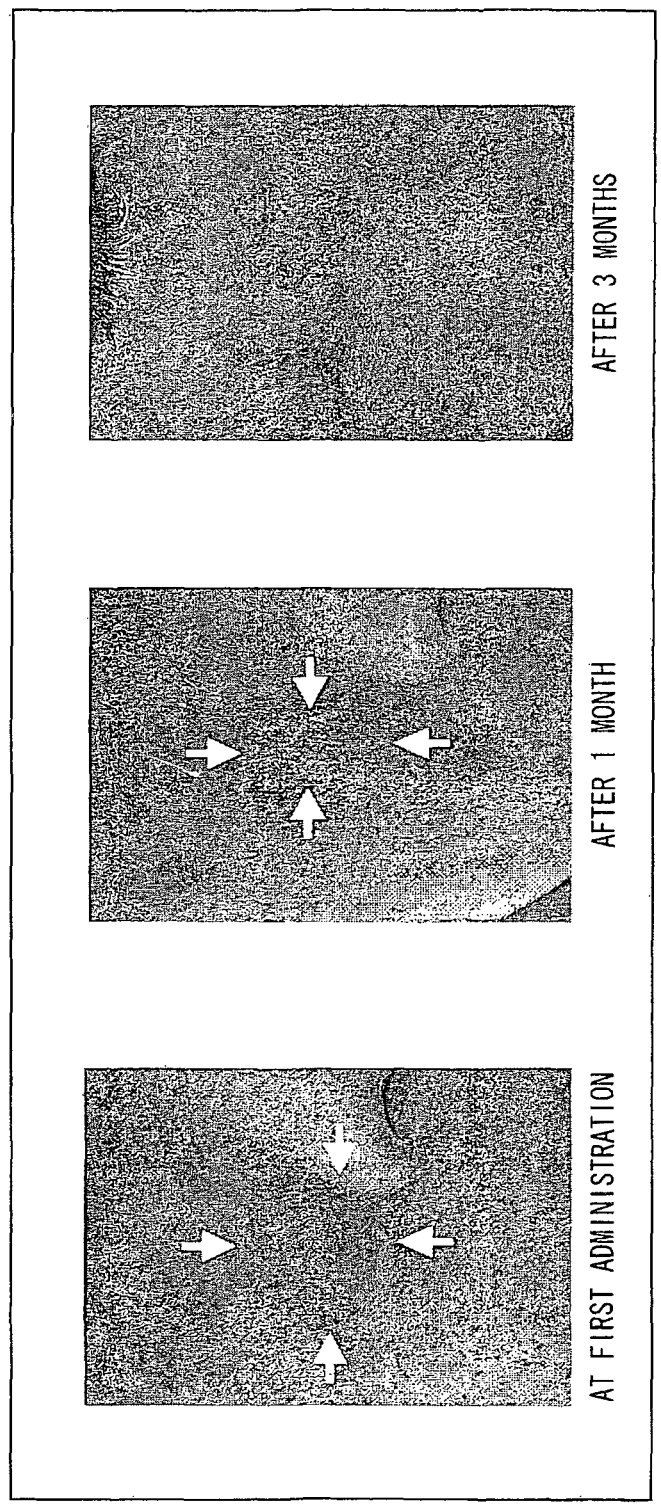
FIG. 8 is a diagram showing photos of follow-ups of an acne patient vaccinated with a vaccine in accordance with certain embodiments of the invention.

100 µl of the prepared PA-MAP solution was hypodermically vaccinated into an upper arm of the acne patient five times at an interval of five days. The acne patient was a patient carrying the patient strain A in the Example 8. FIG. 8 shows the result of observation.

As shown in FIG. 8, before the treatment (at first administration), whole areas of skin bulged and elevated (indicated by arrows in the drawing) due to hypodermic proliferation of acne bacterium, accompanied by inflammation. One month after the first vaccination, although bulge and elevation of acne were still observed, they were divided into two areas and inflammation was improved and localized. Three months after the last vaccination, inflammation was decreasing gradually, acne was turning into scars, and the bulge and elevation were becoming flat. Since it was in the course of the treatment, pigmentary deposit was observed. There was observed no malign phenomenon caused by vaccination.

Case 2

A specimen was collected from the acne patient carrying the patient strain C in the Example 8, and it was confirmed whether the acne patient was infected with *P. acnes* or not by amplifying 16S rDNA of *P. acnes* by PCR. The result showed that the acne patient was *P. acnes* positive. Amplification of 16S rDNA of *P. acnes* was carried out using (i) primer L1 consisting of the same sequence as the primer 9F and (ii) primer R2: 5'-GCACGTAGTTAGCCGGTGCT-3' (SEQ NO. 13) by PCR consisted, of (i) a step at 95° C. for 5 minutes, and thereafter (ii) 35 cycles each consisting of a step at 95° C. for 15 seconds, a step at 55° C. for 20 seconds, and a step at 72° C. for 30 seconds and (iii) a step at 72° C. for seven minutes.

Figure 9:
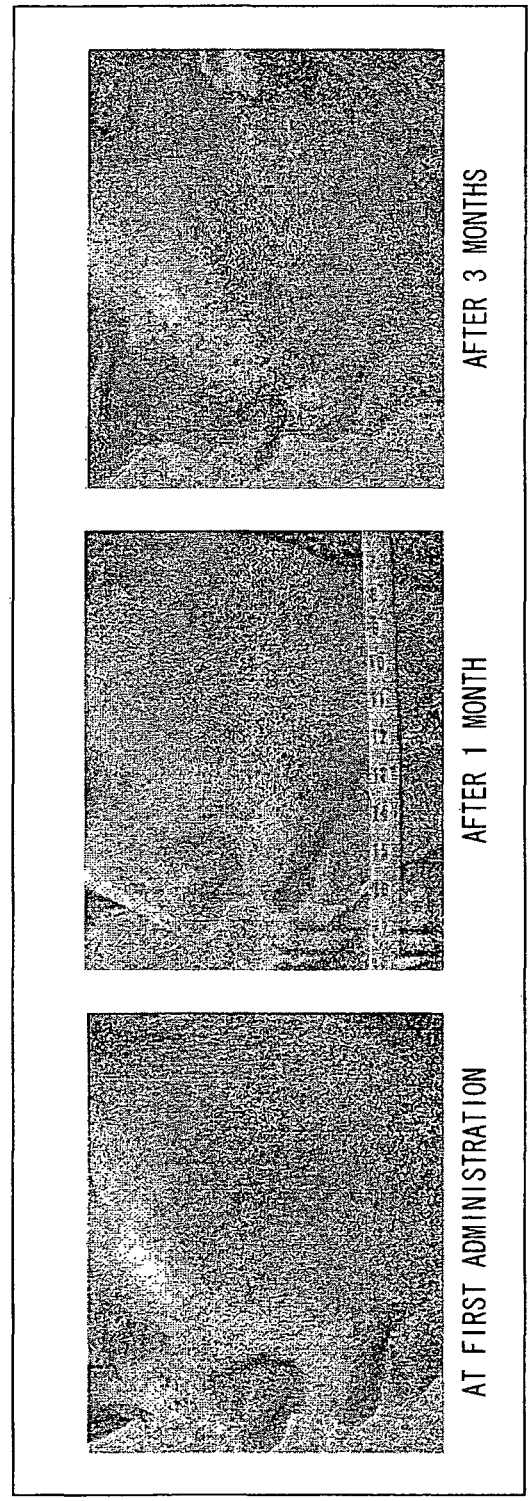
FIG. 9 is a diagram showing photos of follow-ups of another acne patient vaccinated with a vaccine in accordance with certain embodiments of the invention.

300 µl of the prepared PA-MAP solution was hypodermically vaccinated into an upper arm of the acne patient five times at an interval of three days. FIG. 9 shows the result of observation.

As shown in FIG. 9, whole areas of inflammation on the cheek observed before the treatment (at first administration) were improved one month and three months after the first vaccination. There was observed no malign phenomenon caused by vaccination.

Case 3

A specimen was collected from the acne patient carrying the patient strain D in the Example 8, and it was confirmed whether the acne patient was infected with *P. acnes* or not by amplifying 16S rDNA of *P. acnes* by PCR under the same conditions as those in the Case 2. The result showed that the acne patient was *P. acnes* positive.

Figure 10:
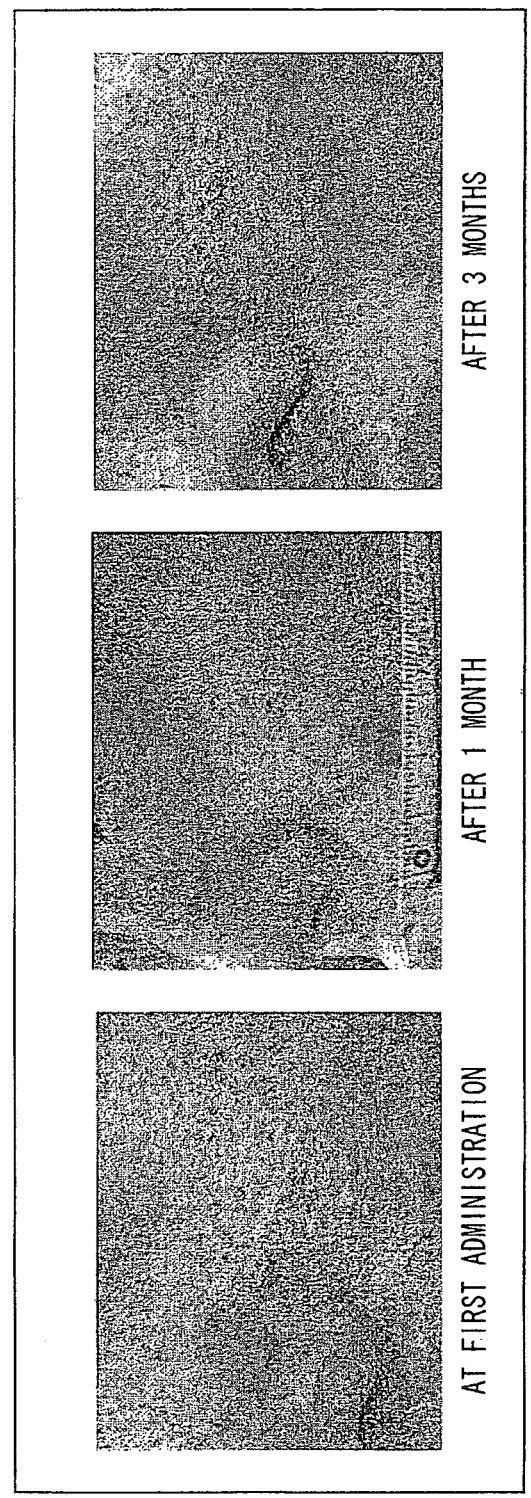
FIG. 10 is a diagram showing photos of follow-ups of still another acne patient vaccinated with a vaccine in accordance with certain embodiments of the invention.

300 μl of the prepared PA-MAP solution was hypodermically vaccinated into an upper arm of the acne patient five times at an interval of three days. FIG. 10 shows the result of observation.

As shown in FIG. 10, whole areas of inflammation around the nose observed before the treatment (at first administration) were improved one month and three months after the first vaccination. There was observed no malign phenomenon caused by vaccination.

Case 4

A specimen was collected from the acne patient carrying the patient strain E in the Example 8, and it was confirmed whether the acne patient was infected with *P. acnes* or not by amplifying 16S rDNA of *P. acnes* by PCR under the same conditions as those in the Case 2. The result showed that the acne patient was *P. acnes* positive.

Figure 11:
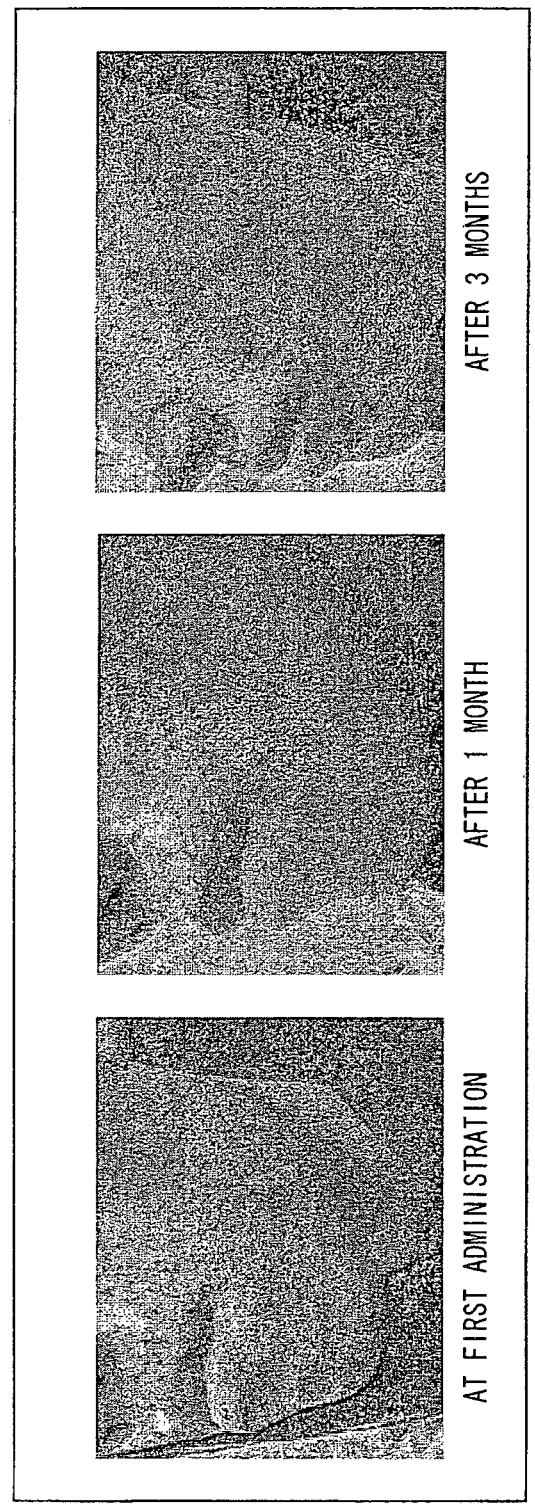
FIG. 11 is a diagram showing photos of follow-ups of yet another acne patient vaccinated with a vaccine in accordance with certain embodiments of the invention.

300 μl of the prepared PA-MAP solution was hypodermically vaccinated into an upper arm of the acne patient five times at an interval of five days. FIG. 11 shows the result of observation.

As shown in FIG. 11, whole areas of inflammation on wide areas of the cheek observed before the treatment (at first administration) were improved one month and three months after the first vaccination. There was observed no malign phenomenon caused by vaccination.

The above results show that the composition containing the peptide PepA and the peptide PepD is effective as a vaccine against *P. acnes*, i.e. an acne vaccine.

Use of the invention enables an immunotherapy for prevention and treatment of acne. Accordingly, the invention is applicable to medical fields, pharmaceutical fields etc. and is very useful.

Example 10

Preparation of Acne Vaccine Including Anti-TNF

A vaccine in accordance with the invention was prepared by combining 500 μg of peptide antigen ABF155 and 500 μg of peptide antigen ABF156 with 50 mg of anti-TNF. The anti-TNF was commercially obtained under the trade name Enbrel. A control vaccine was prepared by combining 500 μg of peptide antigen ABF155 and 500 μg of peptide antigen ABF156 without anti-TNF. Each of the vaccines was administered by subcutaneous injection to patients once per week for a total of twelve weeks. The following blood tests were administered once per month for a total of four months: WBC, RBC, Hb, Hemogram, biochemical tests, IgM, IgG, IgG subtype. Propioni Bacterium Antibody Titer (ELISA assay) and Cytokine Assays were obtained. The assays included the measurement of antibody titers and T-cell responses to the p-acnes bacteria and vaccine peptides employing peripheral blood samples obtained from the patients before and after receipt of the vaccine.

Example 11

Preparation and Administration of Acne Vaccine Including Anti-TNF

A total of eight vaccines were prepared in accordance with the invention and each of the vaccines was administered to a different patient which was inflicted with *Propionibacterium acnes*. Administration consisted of injecting the vaccine into the hip of each patient once per week starting at week 0. Thus, every week subsequent to the initial injection, another injection was administered in the hip of the patient. Photographs were taken at week 0 of an infected area on each of the eight patients and subsequent photographs were taken every four weeks thereafter. The photographs were used to identify the initial number of acne spots and the progression and/or regression of the acne spots over time in response to the vaccine. In addition, blood tests were conducted at week 0 for each of the eight patients and subsequent blood tests were conducted every four weeks thereafter.

Six of the vaccines included the combination of peptide and anti-TNF, and two of the vaccines included peptide only, i.e., in the absence of anti-TNF. At week 0, the initial vaccines, the six peptide/anti-TNF vaccines were prepared by combining 500 μg of peptide antigen ABF155 and 500 μg of peptide antigen ABF156 with 50 mg of anti-TNF (commercially obtained under the trade name Enbrel). At week 0, the initial vaccines, two control vaccines were prepared by combining 500 μg of peptide antigen ABF155 and 500 μg of peptide antigen ABF156 without anti-TNF. For each of the vaccines administered after week 0, the amount of peptide and anti-TNF remained the same. However, it was contemplated that the amount of anti-TNF in each of the vaccines administered after week 0 may be adjusted in accordance with the patients' overall conditions. For example, the original vaccine consisted of 50 mg of anti-TNF and it was contemplated that subsequent injections may have contained either the same, more or less than this amount. In certain embodiments, wherein improvement is observed, e.g., a regression of acne spots, a lower amount of anti-TNF may have been used and wherein the patient's condition is observed to worsen, e.g., an increase in the number of acne spots, a higher amount of anti-TNF may have been used.

The data for each of patients #1 through #8 is shown in Tables A through H, respectively. As shown in Tables A and B (for patients #1 and #2), the administration of the vaccine including peptide and anti-TNF to the acne patients resulted in a complete response. The number of acne spots were significantly reduced (from 8 spots at week 0 to 0 spots at week 12). As shown in Table C (for patient #3), the administration of the vaccine including peptide only to the acne patient resulted in a stable disease response for weeks 0 to 4. The number of acne spots basically remained the same (from 4 spots at week 1 to 4 spots at week 4). However, the injections for the next 12 weeks, i.e., weeks 4 through 16, employed a vaccine with anti-TNF. As a result, the number of acne spots were reduced overall this 12 week period (from 4 spots at week 4 to 0 spots at week 16). As shown in Table D (for patient #4), the administration of the vaccine including peptide and anti-TNF to the acne patient resulted in a partial response. The number of acne spots were significantly reduced (from 7 spots at week 0 to 3 spots at week 10). As shown in Table E (for patient #5), the administration of the vaccine including peptide only to the acne patient resulted in a partial response. The number of acne spots were reduced (from 5 spots at week 0 to 1 spot at week 11). As shown in Tables F and G (for patients #6 and #7), the administration of the vaccine including peptide and anti-TNF to the acne patients resulted in a partial response. The number of acne spots for patients #6 and #7 were reduced (from 14 spots at week 0 to 2 spots at week 12 for patient #6 and from 2 spots at week 0 to 1 spot at week 12 for patient #7). The number of acne spots for As shown in Table H (for patient #8), the administration of the vaccine including peptide and anti-TNF to the acne patient resulted in a stable disease response (the number of spots at week 0 and week 12 was the same, i.e., 5 spots).

Based on the results, it is contemplated that the peptides present in the vaccines were effective as antigen and the anti-TNF was effective to suppress inflammation over-induced by the immune response which was triggered by administration of the vaccine. Further, it was illustrated that the combination of the peptides and anti-TNF was effective enhance vaccine efficacy.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

TABLE A

P-AcneVaccine Pilot Study #1

| Patient Initial | Y.T. | | | | | | |
|---|---|---|---|---|---|---|---|
| ID | 1002000081 | | | | | | |
| Gender | Female | | | | | | |
| Age | 22 | | | | | | |

P-Acne PCR Result

| ABF155 | (+) | | With Anti-TNF 50 mg | | | | |
|---|---|---|---|---|---|---|---|
| ABF156 | (+) | | | | | | |

| Schedule/Weekly | 0 | 1 | 2 | 3 | 4 | 5 | 6 |
|---|---|---|---|---|---|---|---|
| Injection Date (M/D/Y) | Sep. 12, 2013 | Sep. 18, 2013 | Sep. 25, 2013 | Oct. 2, 2013 | Oct. 9, 2013 | Oct. 16, 2013 | Oct. 23, 2013 |
| Injected Site | Hip | Hip | Hip | Hip | Hip | Hip | Hip |
| IgG (870~1700 mg/dl) | 1450 | | | | 1452 | | |
| IgM (35~220 mg/dl) | 226 | | | | 216 | | |
| TNF-α | ND | | | | 151.8 | | |
| Photography | ○ | | | | ○ | | |
| Number of Acne Spots (5 × 5 cm) | 8 | 8 | 2 | 1 | 0 | 0 | 0 |
| Evaluation | | | | | | | |

| Schedule/Weekly | 7 | 8 | 9 | 10 | 11 | 12 |
|---|---|---|---|---|---|---|
| Injection Date (M/D/Y) | Oct. 31, 2013 | Nov. 6, 2013 | Nov. 13, 2013 | Nov. 20, 2013 | Nov. 27, 2013 | Dec. 5, 2013 |
| Injected Site | Hip | Hip | Hip | Hip | Hip | Hip |
| IgG (870~1700 mg/dl) | | 1454 | | | | 1523 |
| IgM (35~220 mg/dl) | | 235 | | | | 245 |
| TNF-α | | 129.6 | | | | 127.2 |
| Photography | | ○ | | | | ○ |
| Number of Acne Spots (5 × 5 cm) | 0 | 0 | 0 | 0 | 0 | 0 |
| Evaluation | | | | | | |

TABLE B

P-AcneVaccine Pilot Study #2

| Patient Initial | R.Y | | | | | | |
|---|---|---|---|---|---|---|---|
| ID | 089000081 | | | | | | |
| Gender | Female | | | | | | |
| Age | 29 | | | | | | |

P-Acne PCR Result

| ABF155 | (+) | | With Anti-TNF 50 mg | | | | |
|---|---|---|---|---|---|---|---|
| ABF156 | (+) | | | | | | |

| Schedule/Weekly | 0 | 1 | 2 | 3 | 4 | 5 | 6 |
|---|---|---|---|---|---|---|---|
| Injection Date (M/D/Y) | Sep. 18, 2013 | Sep. 25, 2013 | Oct. 2, 2013 | Oct. 9, 2013 | Oct. 16, 2013 | Oct. 23, 2013 | Nov. 1, 2013 |
| Injected Site | Hip | Hip | Hip | Hip | Hip | Hip | Hip |
| IgG (870~1700 mg/dl) | 1075 | | | | 1120 | | |
| IgM (35~220 mg/dl) | 238 | | | | 267 | | |

TABLE B-continued

P-AcneVaccine Pilot Study #2

| | | | | | | | |
|---|---|---|---|---|---|---|---|
| TNF-α | 0.8 | | | | 151.8 | | |
| Photography | ○ | | | | ○ | | |
| Number of Acne Spots (5 × 5 cm) Evaluation | 8 | 4 | 2 | 3 | 4 | 2 | 1 |

| Schedule/Weekly | 7 | 8 | 9 | 10 | 11 | 12 |
|---|---|---|---|---|---|---|
| Injection Date (M/D/Y) | Nov. 7, 2013 | Nov. 14, 2013 | Nov. 21, 2013 | Nov. 28, 2013 | Dec. 4, 2013 | Dec. 12, 2013 |
| Injected Site | Hip | Hip | Hip | Hip | Hip | |
| IgG (870~1700 mg/dl) | | 1181 | | | | 991 |
| IgM (35~220 mg/dl) | | 293 | | | | 252 |
| TNF-α | | 172.7 | | | | 153.2 |
| Photography | | ○ | | | | ○ |
| Number of Acne Spots (5 × 5 cm) Evaluation | 0 | 2 | 1 | 1 | 0 | 0 |

TABLE C

P-AcneVaccine Pilot Study #3

| | |
|---|---|
| Patient Initial | H.U. |
| ID | 1007000081 |
| Gender | Male |
| Age | 22 |

| P-Acne PCR Result | | | |
|---|---|---|---|
| ABF155 | (+) | Without Anti-TNF 50 mg | ✗Folliculitis s/o Bacteriological test (Dec. 26, 2013) Result: coagulase negative *Staphylococcus* 1+ |
| ABF156 | (+) | | |

| Schedule/Weekly | 0 | 1 | 2 | 3 | 4 | 5 |
|---|---|---|---|---|---|---|
| Injection Date (M/D/Y) | Sep. 20, 2013 | Sep. 27, 2013 | Oct. 3, 2013 | Oct. 11, 2013 | Oct. 17, 2013 | Oct. 25, 2013 |
| Injected Site | Hip | Hip | Hip | Hip | Hip | Hip |
| IgG (870~1700 mg/dl) | 1524 | | | | 1570 | |
| IgM (35~220 mg/dl) | 162 | | | | 197 | |
| TNF-α | 1.1 | | | | 1.4 | |
| Photography | ○ | | | | ○ | |
| Number of Acne Spots (5 × 5 cm) Evaluation | | 4 | 3 | 4 | 4 | 6 |

With Anti-TNF→

| Schedule/Weekly | 6 | 7 | 8 | 9 | 10 | 11 |
|---|---|---|---|---|---|---|
| Injection Date (M/D/Y) | Nov. 1, 2013 | Nov. 8, 2013 | Nov. 14, 2013 | Nov. 25, 2013 | Dec. 5, 2013 | Dec. 12, 2013 |
| Injected Site | Hip | Hip | Hip | Hip | Hip | Hip |
| IgG (870~1700 mg/dl) | | | 1508 | | | |
| IgM (35~220 mg/dl) | | | 170 | | | |
| TNF-α | | | 151.2 | | | |
| Photography | | | ○ | | | |
| Number of Acne Spots (5 × 5 cm) Evaluation | 5 | 4 | 4 | 5 | 7 | 7 |

With Anti-TNF→

| Schedule/Weekly | 12 | 13 | 14 | 15 | 16 |
|---|---|---|---|---|---|
| Injection Date (M/D/Y) | Dec. 26, 2013 | Jan. 10, 2014 | Jan. 17, 2014 | Jan. 27, 2014 | Feb. 4, 2014 |
| Injected Site | Hip | Hip | Hip | Hip | Hip |
| IgG (870~1700 mg/dl) | 1467 | | | | |

TABLE C-continued

P-AcneVaccine Pilot Study #3

| | | | | | | |
|---|---|---|---|---|---|---|
| IgM (35~220 mg/dl) | 162 | | | | | |
| TNF-α | 124.5 | | | | | |
| Photography | ○ | | | | | ○ |
| Number of Acne Spots (5 × 5 cm) | 14 | 14 | 9 | 0 | 0 | |
| Evaluation | | | | | | |

TABLE D

P-AcneVaccine Pilot Study #4

| Patient Initial | A.Y |
|---|---|
| ID | 096000081 |
| Gender | Female |
| Age | 35 |

P-Acne PCR Result

| ABF155 | (+) | With Anti-TNF 50 mg |
|---|---|---|
| ABF156 | (+) | |

| Schedule/Weekly | 0 | 1 | 2 | 3 | 4 | 5 | 6 |
|---|---|---|---|---|---|---|---|
| Injection Date (M/D/Y) | Dec. 27, 2013 | Jan. 8, 2014 | Jan. 17, 2014 | Jan. 24, 2014 | Jan. 31, 2014 | Feb. 7, 2014 | Feb. 14, 2014 |
| Injected Site | Hip | Hip | Hip | Hip | Hip | Hip | Hip |
| IgG (870~1700 mg/dl) | 1365 | | | | 1271 | | |
| IgM (35~220 mg/dl) | 104 | | | | 101 | | |
| TNF-α | 4.6 | | | | 147.4 | | |
| Photography | ○ | | | | ○ | | |
| Number of Acne Spots (5 × 5 cm) | 7 | 5 | 5 | 4 | 3 | 5 | 4 |
| Evaluation | | | | | | | |

| Schedule/Weekly | 7 | 8 | 9 | 10 | 11 | 12 |
|---|---|---|---|---|---|---|
| Injection Date (M/D/Y) | Feb. 27, 2014 | Mar. 7, 2014 | Mar. 14, 2014 | Mar. 28, 2014 | Apr. 4, 2014 | |
| Injected Site | Hip | Hip | Hip | Hip | Hip | |
| IgG (870~1700 mg/dl) | | 1368 | | | | |
| IgM (35~220 mg/dl) | | 97 | | | | |
| TNF-α | | 115.8 | | | | |
| Photography | | | ○ | | | |
| Number of Acne Spots (5 × 5 cm) | 3 | 2 | 3 | 3 | | |
| Evaluation | | | | | | |

TABLE E

P-AcneVaccine Pilot Study #5

| Patient Initial | M.T |
|---|---|
| ID | 102500081 |
| Gender | Female |
| Age | 62 |

P-Acne PCR Result

| ABF155 | (+) | Without Anti-TNF 50 mg |
|---|---|---|
| ABF156 | (+) | |

| Schedule/Weekly | 0 | 1 | 2 | 3 | 4 | 5 | 6 |
|---|---|---|---|---|---|---|---|
| Injection Date (M/D/Y) | Nov. 13, 2013 | Nov. 20, 2013 | Nov. 27, 2013 | Dec. 4, 2013 | Dec. 11, 2013 | Dec. 18, 2013 | Dec. 25, 2013 |
| Injected Site | Hip | Hip | Hip | Hip | Hip | Hip | Hip |
| IgG (870~1700 mg/dl) | | | | | 1825 | | |
| IgM (35~220 mg/dl) | | | | | 92 | | |
| TNF-α | 3.5 | | | | 2.1 | | |
| Photography | ○ | | | | ○ | | |

TABLE E-continued

P-AcneVaccine Pilot Study #5

| | | | | | | | |
|---|---|---|---|---|---|---|---|
| Number of Acne Spots (5 × 5 cm) Evaluation | 5 | 0 | 0 | 1 | 0 | 2 | 2 |

| | Schedule/Weekly | 7 | 8 | 9 | 10 | 11 | 12 |
|---|---|---|---|---|---|---|---|
| | Injection Date (M/D/Y) | Jan. 8, 2014 | Jan. 15, 2013 | Jan. 22, 2014 | Jan. 28, 2014 | Feb. 5, 2014 | Feb. 13, 2014 |
| | Injected Site | Hip | Hip | Hip | Hip | Hip | |
| | IgG (870~1700 mg/dl) | | 1846 | | | | |
| | IgM (35~220 mg/dl) | | 85 | | | | |
| | TNF-α | | 2.3 | | | | |
| | Photography | | ○ | | | | ○ |
| | Number of Acne Spots (5 × 5 cm) Evaluation | 2 | 3 | 3 | 1 | 1 | |

TABLE F

P-AcneVaccine Pilot Study #6

| Patient Initial | A.Y |
|---|---|
| ID | 103400081 |
| Gender | Female |
| Age | 42 |

P-Acne PCR Result

| ABF155 | (+) | With Anti-TNF 50 mg |
|---|---|---|
| ABF156 | (−) | |

| Schedule/Weekly | 0 | 1 | 2 | 3 | 4 | 5 | 6 |
|---|---|---|---|---|---|---|---|
| Injection Date (M/D/Y) | Nov. 29, 2013 | Dec. 6, 2013 | Dec. 13, 2013 | Dec. 20, 2013 | Dec. 27, 2013 | Jan. 10, 2014 | Jan. 17, 2014 |
| Injected Site | Hip | Hip | Hip | Hip | Hip | Hip | Hip |
| IgG (870~1700 mg/dl) | 1135 | | | | 984 | | |
| IgM (35~220 mg/dl) | 222 | | | | 170 | | |
| TNF-α | 2.0 | | | | 81.6 | | |
| Photography | ○ | | | | ○ | | |
| Number of Acne Spots (5 × 5 cm) Evaluation | 14 | 14 | 10 | 14 | 14 | 12 | 10 |

| | Schedule/Weekly | 7 | 8 | 9 | 10 | 11 | 12 |
|---|---|---|---|---|---|---|---|
| | Injection Date (M/D/Y) | Jan. 24, 2014 | Jan. 31, 2014 | Feb. 6, 2014 | Feb. 13, 2014 | Feb. 21, 2014 | Feb. 28, 2014 |
| | Injected Site | Hip | Hip | Hip | Hip | Hip | Hip |
| | IgG (870~1700 mg/dl) | | 1074 | | | | 1074 |
| | IgM (35~220 mg/dl) | | 194 | | | | 185 |
| | TNF-α | | 107.0 | | | | 124.5 |
| | Photography | | ○ | | | | ○ |
| | Number of Acne Spots (5 × 5 cm) Evaluation | 10 | 7 | 5 | 6 | 5 | 2 |

TABLE G

P-AcneVaccine Pilot Study #7

| Patient Initial | A.K |
|---|---|
| ID | 106100081 |
| Gender | Female |
| Age | 40 |

P-Acne PCR Result

| ABF155 | (+) | With Anti-TNF 50 mg |
|---|---|---|
| ABF156 | (+) | |

| Schedule/Weekly | 0 | 1 | 2 | 3 | 4 | 5 | 6 |
|---|---|---|---|---|---|---|---|
| Injection Date (M/D/Y) | Dec. 25, 2013 | Jan. 8, 2014 | Jan. 17, 2014 | Jan. 22, 2014 | Jan. 29, 2014 | Feb. 5, 2014 | Feb. 12, 2014 |
| Injected Site | Hip | Hip | Hip | Hip | Hip | Hip | Hip |
| IgG (870~1700 mg/dl) | 1614 | | | | 1532 | | |

TABLE G-continued

P-AcneVaccine Pilot Study #7

| | | | | | | | |
|---|---|---|---|---|---|---|---|
| IgM (35~220 mg/dl) | 36 | | | | 35 | | |
| TNF-α | ND | | | | 158.9 | | |
| Photography | ○ | | | | ○ | | |
| Number of Acne Spots (5 × 5 cm) Evaluation | 2 | 1 | 0 | 0 | 1 | 1 | 1 |

| Schedule/Weekly | 7 | 8 | 9 | 10 | 11 | 12 |
|---|---|---|---|---|---|---|
| Injection Date (M/D/Y) | Feb. 21, 2014 | Feb. 26, 2014 | Mar. 5, 2014 | Mar. 12, 2014 | Mar. 19, 2014 | Mar. 26, 2014 |
| Injected Site | Hip | Hip | Hip | Hip | Hip | Hip |
| IgG (870~1700 mg/dl) | | 1457 | | | | |
| IgM (35~220 mg/dl) | | 36 | | | | |
| TNF-α | | 260.5 | | | | 133.1 |
| Photography | | ○ | | | | ○ |
| Number of Acne Spots (5 × 5 cm) Evaluation | 0 | 0 | 0 | 2 | 1 | 1 |

TABLE H

P-AcneVaccine Pilot Study #8

| | |
|---|---|
| Patient Initial | M.O |
| ID | 105500081 |
| Gender | Female |
| Age | 23 |

P-Acne PCR Result

| | | |
|---|---|---|
| ABF155 | (+) | With Anti-TNF 50 mg |
| ABF156 | (−) | |

| Schedule/Weekly | 0 | 1 | 2 | 3 | 4 | 5 | 6 |
|---|---|---|---|---|---|---|---|
| Injection Date (M/D/Y) | Dec. 11, 2013 | Dec. 18, 2013 | Dec. 24, 2013 | Jan. 8, 2014 | Jan. 15, 2014 | Jan. 22, 2014 | Jan. 29, 2014 |
| Injected Site | Hip | Hip | Hip | Hip | Hip | Hip | Hip |
| IgG (870~1700 mg/dl) | 1348 | | | | 1546 | | |
| IgM (35~220 mg/dl) | 170 | | | | 218 | | |
| TNF-α | 0.7 | | | | 97.3 | | |
| Photography | ○ | | | | ○ | | |
| Number of Acne Spots (5 × 5 cm) Evaluation | 5 | 5 | 2 | 5 | 4 | 5 | 2 |

| Schedule/Weekly | 7 | 8 | 9 | 10 | 11 | 12 |
|---|---|---|---|---|---|---|
| Injection Date (M/D/Y) | Feb. 5, 2014 | Feb. 12, 2014 | Feb. 20, 2014 | Feb. 26, 2014 | Mar. 5, 2014 | Mar. 12, 2014 |
| Injected Site | Hip | Hip | Hip | Hip | Hip | Hip |
| IgG (870~1700 mg/dl) | | 1414 | | | | 1597 |
| IgM (35~220 mg/dl) | | 207 | | | | 237 |
| TNF-α | | 154.8 | | | | 159.0 |
| Photography | | ○ | | | | ○ |
| Number of Acne Spots (5 × 5 cm) Evaluation | 10 | 9 | 9 | 7 | 5 | 5 |

The invention claimed is:

1. A composition to reduce inflammation in a patient with a *Propionibacterium acnes* infection, comprising:
   a peptide consisting of the amino acid sequence of SEQ NO. 1; and
   a TNF inhibitor.

2. The composition of claim 1, wherein the peptide is in a form of a multivalent antigen peptide obtained by binding a plurality of the peptide consisting of the amino acid sequence of SEQ NO. 1 by a linker.

3. A vaccine to reduce inflammation in a patient with a *Propionibacterium acnes* infection, comprising:
   a peptide consisting of the amino acid sequence of SEQ NO. 1; and
   a TNF inhibitor.

4. The vaccine of claim 3, wherein the peptide is in a form of a multivalent antigen peptide obtained by binding a plurality of the peptide consisting of the amino acid sequence of SEQ NO. 1 by a linker.

5. The vaccine of claim 4, wherein the peptide and the TNF inhibitor are combined in the form of a composition.

* * * * *

SEQUENCE LISTING

<160> NUMBER OF SEQ ID NOS: 16

<210> SEQ ID NO 1
<211> LENGTH: 14
<212> TYPE: PRT
<213> ORGANISM: Propionibacterium acnes

<400> SEQUENCE: 1

Ala Ile Gln Glu Lys Tyr Gly Asp Asp Arg Glu Arg Ala Gly
1               5                   10

<210> SEQ ID NO 2
<211> LENGTH: 42
<212> TYPE: DNA
<213> ORGANISM: Propionibacterium acnes

<400> SEQUENCE: 2
gccatccagg aaaagtacgg cgacgacagg gaacgtgccg gc                42

<210> SEQ ID NO 3
<211> LENGTH: 13
<212> TYPE: PRT
<213> ORGANISM: Propionibacterium acnes

<400> SEQUENCE: 3

Lys Asp Ala Asp Lys Asp Asn Pro Thr Tyr Gln Lys Val
1               5                   10

<210> SEQ ID NO 4
<211> LENGTH: 39
<212> TYPE: DNA
<213> ORGANISM: Propionibacterium acnes

<400> SEQUENCE: 4
aaggacgctg acaaagacaa cccgacgtac cagaaggtc                   39

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtttgatcct ggctca                                            16

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taccagggta tctaatcc                                          18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtattaccgc ggctgctgg                                         19

<210> SEQ ID NO 8
<211> LENGTH: 511
<212> TYPE: DNA
<213> ORGANISM: Propionibacterium acnes

<400> SEQUENCE: 8

-continued

```
agagtttgat cctggctcag gacgaacgct ggcggcgtgc ttaacacatg caagtcgaac    60
ggaaaggccc tgcttttgtg gggtgctcga gtggcgaacg ggtgagtaac acgtgagtaa   120
cctgcccttg actttgggat aacttcagga aactggggct aataccggat aggagctcct   180
gctgcatggt gggggttgga aagtttcggc ggttggggat ggactcgcgg cttatcagct   240
tgttggtggg gtagtggctt accaaggctt tgacgggtag ccggcctgag agggtgaccg   300
gccacattgg gactgagata cggcccagac tcctacggga ggcagcagtg gggaatattg   360
cacaatgggc ggaagcctga tgcagcaacg ccgcgtgcgg gatgacggcc ttcgggttgt   420
aaaccgcttt cgcctgtgac gaagcgtgag tgacggtaat gggtaaagaa gcaccggcta   480
actacgtgcc agcagccgcg gtgatacgta g                                  511
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9

```
gatgaaagcc atccaggaaa                                                20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10

```
gcacacgaaa caacgctaga                                                20
```

<210> SEQ ID NO 11
<211> LENGTH: 17
<212> TYPE: PRT
<213> ORGANISM: Propionibacterium acnes

<400> SEQUENCE: 11

Gly Arg Lys Pro Asp Thr Asn Lys Arg Ser Trp His Arg Lys Ala Ser
1               5                   10                  15

Arg

<210> SEQ ID NO 12
<211> LENGTH: 22
<212> TYPE: PRT
<213> ORGANISM: Propionibacterium acnes

<400> SEQUENCE: 12

Ile Asp Gln Val Arg Glu Tyr Arg His Arg Asp Asp Asp Asp Glu
1               5                   10                  15

Asp Pro Gly Glu Asp Gly
            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 13
gcacgtagtt agccggtgct                                                    20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtgctgtcg tcaataacaa cttc                                               24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagtggcca gagacgatct                                                    20

<210> SEQ ID NO 16
<211> LENGTH: 504
<212> TYPE: DNA
<213> ORGANISM: Propionibacterium acnes

<400> SEQUENCE: 16
gtttgatcct ggctcaggac gaacgctggc ggcgtgctta acacatgcaa gtcgaacgga        60
aaggccctgc ttttgtgggg tgctcgagtg gcgaacgggt gagtaacacg tgagtaacct       120
gcccttgact ttgggataac ttcaggaaac tggggctaat accggatagg agctcctgct       180
gcatggtggg ggttggaaag tttcggcggt tggggatgga ctcgcggctt atcagcttgt       240
tggtggggta gtggcttacc aaggctttga cgggtagccg gcctgagagg gtgaccggcc       300
acattgggac tgagatacgg cccagactcc tacgggaggc agcagtgggg aatattgcac       360
aatgggcgga agcctgatgc agcaacgccg cgtgcgggat gacggccttc gggttgtaaa       420
ccgctttcgc ctgtgacgaa gcgtgagtga cggtaatggg taaagaagca ccggctaact       480
acgtgccagc agccgcggtg atac                                              504
```